(12) United States Patent
Watanabe et al.

(10) Patent No.: US 10,918,265 B2
(45) Date of Patent: Feb. 16, 2021

(54) IMAGE PROCESSING APPARATUS FOR ENDOSCOPE AND ENDOSCOPE SYSTEM

(71) Applicant: OLYMPUS CORPORATION, Tokyo (JP)

(72) Inventors: Takanori Watanabe, Fuchu (JP); Jin Ito, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 346 days.

(21) Appl. No.: 16/012,946

(22) Filed: Jun. 20, 2018

(65) Prior Publication Data
US 2018/0310809 A1 Nov. 1, 2018

Related U.S. Application Data

(63) Continuation of application No. PCT/JP2016/086269, filed on Dec. 6, 2016.

(30) Foreign Application Priority Data

Dec. 22, 2015 (JP) .............................. JP2015-250036

(51) Int. Cl.
*A61B 1/00* (2006.01)
*A61B 1/045* (2006.01)
(Continued)

(52) U.S. Cl.
CPC ........ *A61B 1/00181* (2013.01); *A61B 1/0005* (2013.01); *A61B 1/00009* (2013.01);
(Continued)

(58) Field of Classification Search
None
See application file for complete search history.

(56) References Cited

U.S. PATENT DOCUMENTS 5,940,126 A * 8/1999 Kimura ................ H04N 5/2253
348/294
2011/0273549 A1 11/2011 Kase et al.
(Continued)

FOREIGN PATENT DOCUMENTS

CN 102469930 A 5/2012
EP 2425760 A1 3/2012
(Continued)

OTHER PUBLICATIONS

International Search Report dated Mar. 7, 2017 issued in PCT/JP2016/086269.

*Primary Examiner* — Timothy J Neal
(74) *Attorney, Agent, or Firm* — Scully, Scott, Murphy & Presser, P.C.

(57) ABSTRACT

A video processor includes: an image processing section including a front image enhancement processing section configured to perform first enhancement processing on a front image acquired from a front area in a subject by using an endoscope including an insertion portion which is inserted into the subject, and a side image enhancement processing section configured to perform second enhancement processing on a side image acquired from a side area located lateral to the front area by using the endoscope; and a control section configured to individually set an enhancement level of enhancement processing performed by the front image enhancement processing section and an enhancement level of enhancement processing performed by the side image enhancement processing section.

13 Claims, 16 Drawing Sheets

(51) Int. Cl.
*G06T 5/00* (2006.01)
*A61B 1/06* (2006.01)
*A61B 1/05* (2006.01)
*A61B 1/07* (2006.01)

(52) U.S. Cl.
CPC ...... *A61B 1/00048* (2013.01); *A61B 1/00096* (2013.01); *A61B 1/00179* (2013.01); *A61B 1/045* (2013.01); *A61B 1/05* (2013.01); *A61B 1/0669* (2013.01); *A61B 1/07* (2013.01); *G06T 5/00* (2013.01); *A61B 1/0661* (2013.01); *G06T 5/002* (2013.01); *G06T 2207/10024* (2013.01); *G06T 2207/10068* (2013.01); *G06T 2207/20012* (2013.01); *G06T 2207/20021* (2013.01); *G06T 2207/30101* (2013.01)

(56) References Cited

U.S. PATENT DOCUMENTS

| | | | | |
|---|---|---|---|---|
| 2011/0275889 | A1* | 11/2011 | Kase | A61B 1/00177 600/103 |
| 2012/0053407 | A1* | 3/2012 | Levy | G02B 23/2423 600/109 |
| 2014/0142381 | A1* | 5/2014 | Bae | G02B 23/2484 600/109 |
| 2014/0204187 | A1* | 7/2014 | Sasaki | G06T 7/33 348/65 |
| 2014/0330078 | A1* | 11/2014 | Hwang | A61B 1/0623 600/111 |
| 2014/0346332 | A1* | 11/2014 | Honda | G02B 23/243 250/227.21 |
| 2016/0015258 | A1* | 1/2016 | Levin | A61B 1/00009 600/109 |
| 2017/0014017 | A1 | 1/2017 | Ohara et al. | |
| 2017/0258302 | A1* | 9/2017 | Takahashi | A61B 1/00181 |
| 2019/0356829 | A1* | 11/2019 | Sidar | A61B 1/05 |

FOREIGN PATENT DOCUMENTS

| | | |
|---|---|---|
| EP | 2497406 A1 | 9/2012 |
| EP | 3111824 A1 | 1/2017 |
| JP | S61-31125 A | 2/1986 |
| JP | H07-194598 A | 8/1995 |
| JP | 2008-023017 A | 2/2008 |
| JP | 2011-139732 A | 7/2011 |
| JP | 2011-152202 A | 8/2011 |
| JP | 2013-153991 A | 8/2013 |
| WO | WO 2011/055613 A1 | 5/2011 |
| WO | WO 2011/055614 A1 | 5/2011 |
| WO | WO 2011/092951 A1 | 8/2011 |
| WO | WO 2015/151973 A1 | 10/2015 |

* cited by examiner

IMAGE PROCESSING APPARATUS FOR ENDOSCOPE AND ENDOSCOPE SYSTEM

CROSS REFERENCE TO RELATED APPLICATION

This application is a continuation application of PCT/JP2016/086269 filed on Dec. 6, 2016 and claims benefit of Japanese Application No. 2015-250036 filed in Japan on Dec. 22, 2015, the entire contents of which are incorporated herein by this reference.

BACKGROUND OF THE INVENTION

1. Field of the Invention

The present invention relates to an image processing apparatus for endoscope and an endoscope system, and especially relates to an image processing apparatus for endoscope and an endoscope system which are capable of simultaneously observing more than one visual field image.

2. Description of Related Art

An endoscope system is widely used in a medical field, an industrial field, and other fields, the system including an endoscope configured to pick up an image of an object inside a subject, and an image processing apparatus configured to generate an observed image of the object, an image of which has been picked up by the endoscope. A user, for example an operator, of the endoscope system can insert an insertion portion of the endoscope into a subject so as to perform observation, treatment, and the like, inside the subject.

Further, the endoscope system is provided with a function of enhancing a whole observed image in accordance with an observation scene during examination, a purpose, preference of the operator, or the like. The image enhancement processing is performed for such a purpose as facilitating viewing of a blood vessel in the observed image or facilitating observation of a structure of a lesion, and the image enhancement includes structure enhancement and hue enhancement. For example, Japanese Patent Application Laid-Open Publication No. 2011-139732 proposes an endoscope apparatus that displays an observed image with enhanced contrast.

In the endoscope system having the image enhancement function, the operator can select a set value suitable for the purpose among a plurality of set values for image enhancement, previously set in the system. The endoscope system performs image enhancement processing on the observed image based on the selected set value, so that the operator can conduct endoscopy by looking at the enhanced objected image suitable for the purpose.

For example, the operator can execute the image enhancement processing at a high enhancement level when confirming a location of a blood vessel prior to treatment, and the operator can execute the image enhancement processing at a low enhancement level so as not to increase noise when recording the observed image.

Among the endoscope systems, an endoscope system in which a subject can be observed in a wide visual field so as to prevent oversight in a lesion and the like, for example, a wide-angle endoscope system having more than one visual field such as a front visual field image and a side visual field image exists. Such a wide-angle endoscope system is also provided with the function of enhancing all displayed visual field images.

In the case of endoscopy using the wide-angle endoscope system, the front visual field and the side visual field have different roles. For example, the operator uses the side visual field image to find a lesion, while the operator uses the front visual field image in performing detailed examination on the lesion.

SUMMARY OF THE INVENTION

An image processing apparatus for endoscope according to one aspect of the present invention is provided with: a processor; and an image processing section including a front image enhancement processing section configured to perform first enhancement processing on a front image acquired from a front area in a subject by using an endoscope including an insertion portion which is inserted into the subject, and a side image enhancement processing section configured to perform second enhancement processing on a side image acquired from a side area located lateral to the front area, the processor individually sets a first enhancement level of the first enhancement processing performed by the front image enhancement processing section and a second enhancement level of the second enhancement processing performed by the side image enhancement processing section, and the processor sets the second enhancement level of the side image such that an image enhancement becomes stronger as distance from the front image increases.

The endoscope system according to one aspect of the present invention is an endoscope system including: the image processing apparatus for endoscope according to the one aspect; a front observation optical system configured to form an optical image of the front area; a side observation optical system configured to form an optical image of the side area; and an image pickup device configured to pick up the optical image of the front area and the optical image of the side area, the image processing apparatus for endoscope includes a separation section configured to separate the front image and the side image from an image pickup signal outputted from the image pickup device, and the front image separated by the separation section is inputted into the front image enhancement processing section and the side image is inputted into the side image enhancement processing section.

An endoscope system according to one aspect of the present invention includes: the image processing apparatus for endoscope according to the one aspect; a front observation optical system configured to form an optical image of the front area; a side observation optical system configured to form an optical image of the side area; a first image pickup device configured to pick up the optical image of the front area and generate the front image; and a second image pickup device formed as a separate body from the first image pickup device and configured to pick up the optical image of the side area and generate the side image.

DETAILED DESCRIPTION OF PREFERRED EMBODIMENTS

Embodiments of the present invention will be described below with reference to the drawings.

First Embodiment (Configuration)

Figure 1:
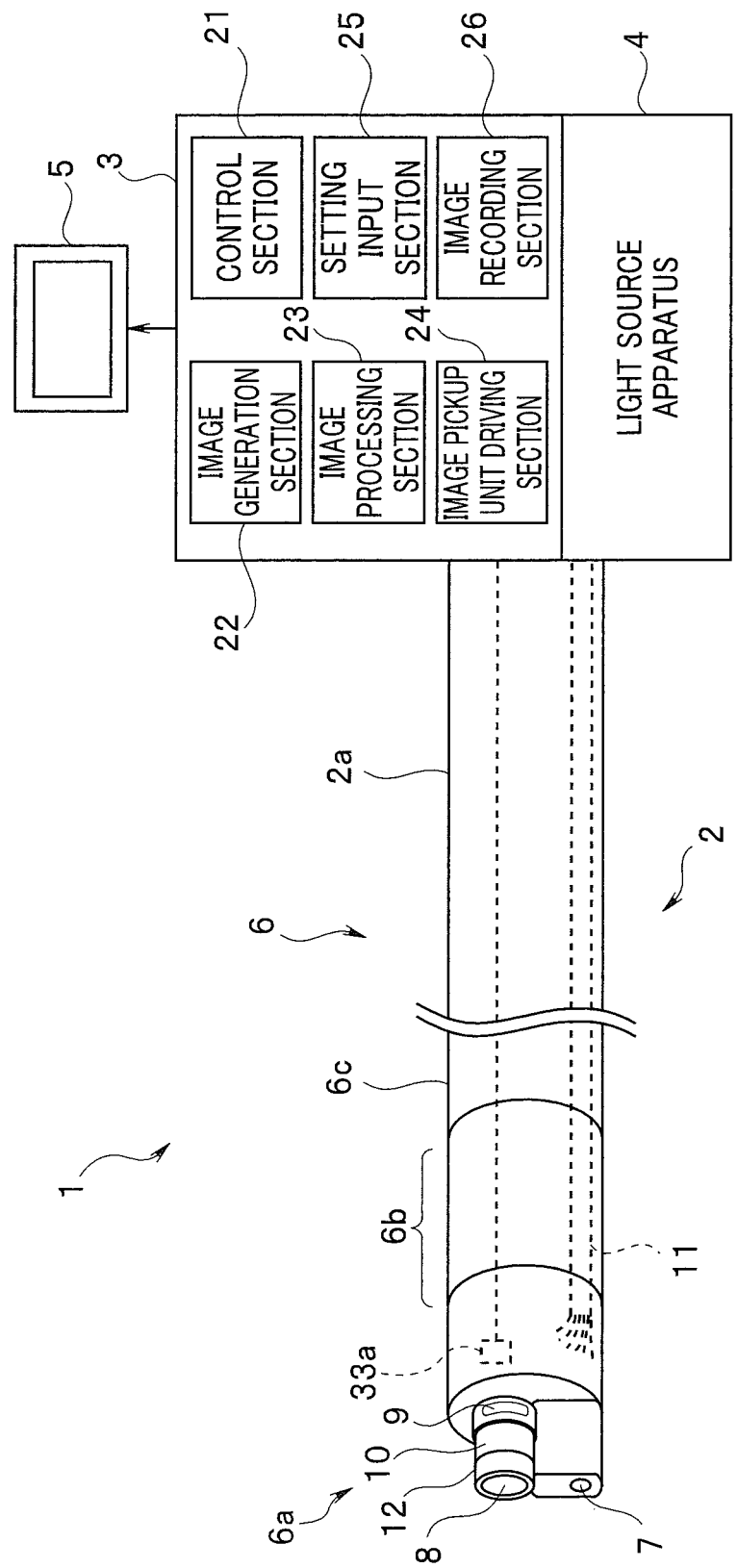
FIG. 1 is a configuration diagram showing a configuration of an endoscope system according to a first embodiment of the present invention.
Figure 2:
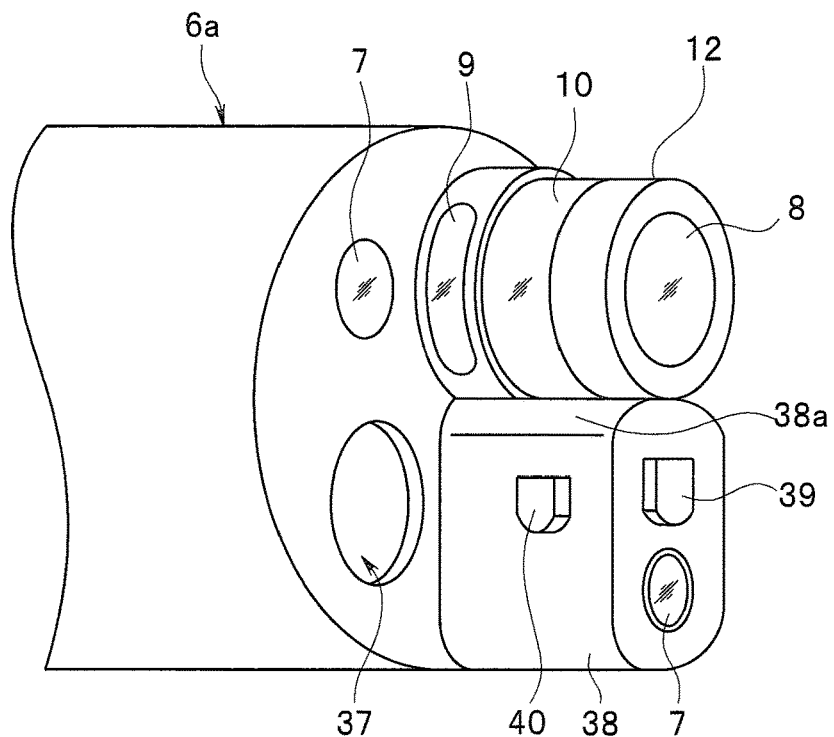
FIG. 2 is a perspective view showing a configuration of a distal end portion of an insertion portion of an endoscope according to the first embodiment of the present invention.
Figure 3:
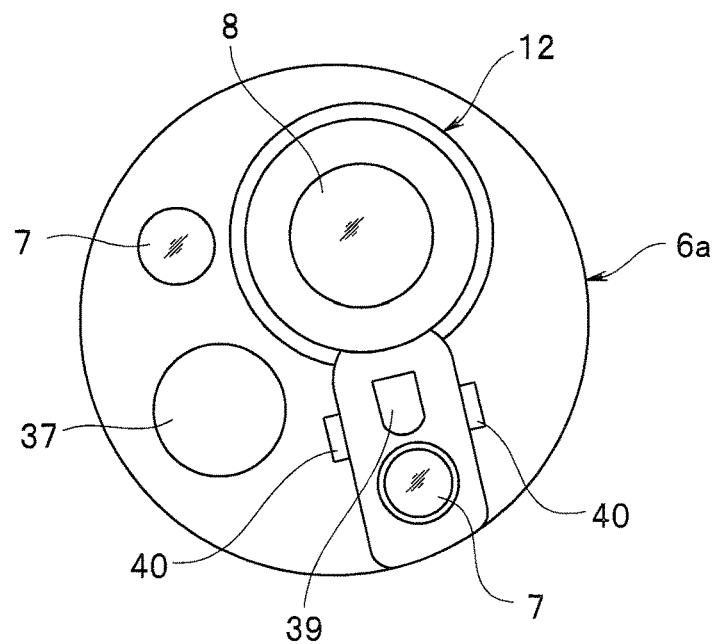
FIG. 3 is a front view showing a configuration of a distal end portion of the insertion portion of the endoscope according to the first embodiment of the present invention.
Figure 4:
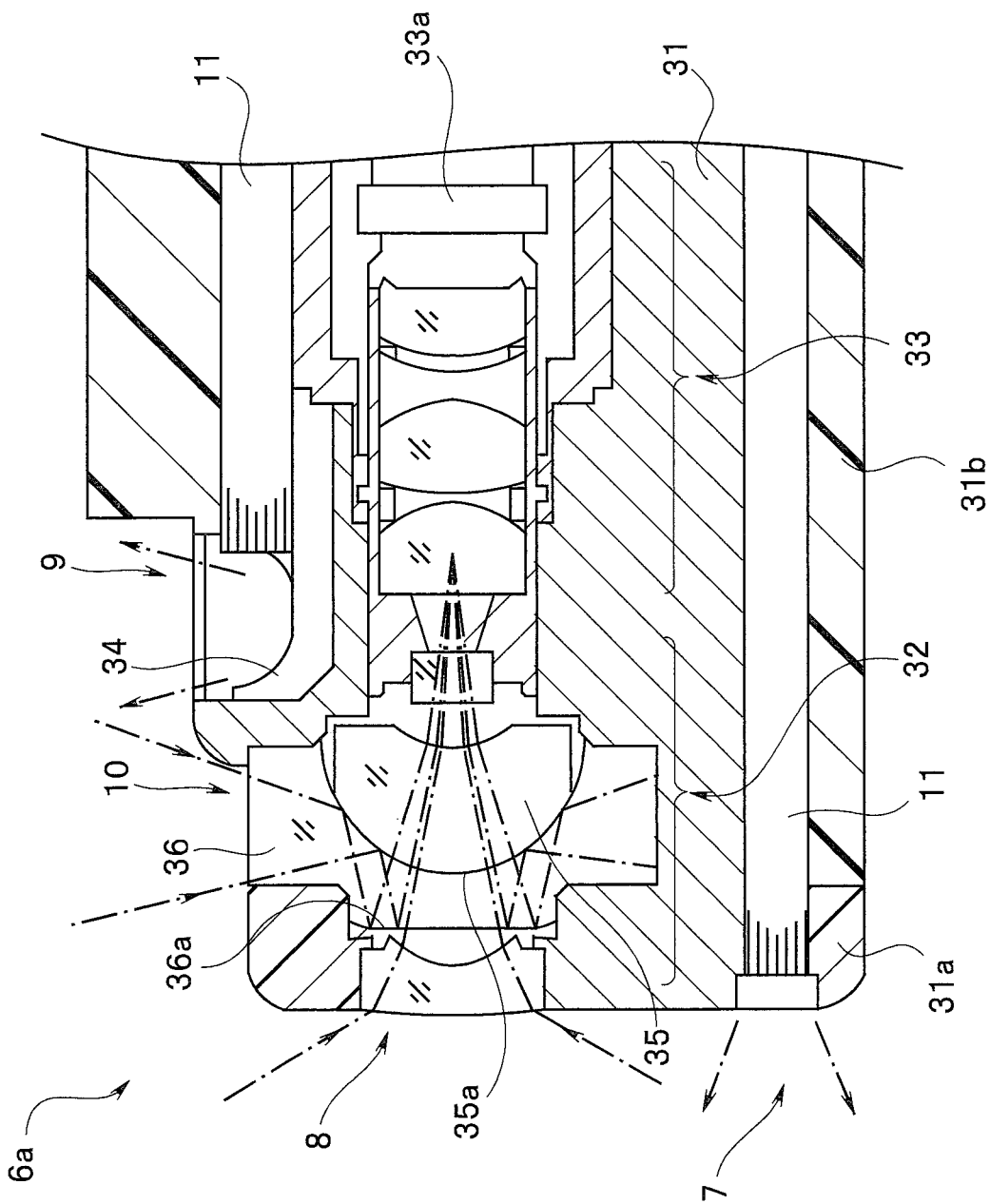
FIG. 4 is a sectional view of a distal end portion 6a along an axial direction of an insertion portion 6 according to the first embodiment of the present invention.
Figure 5:
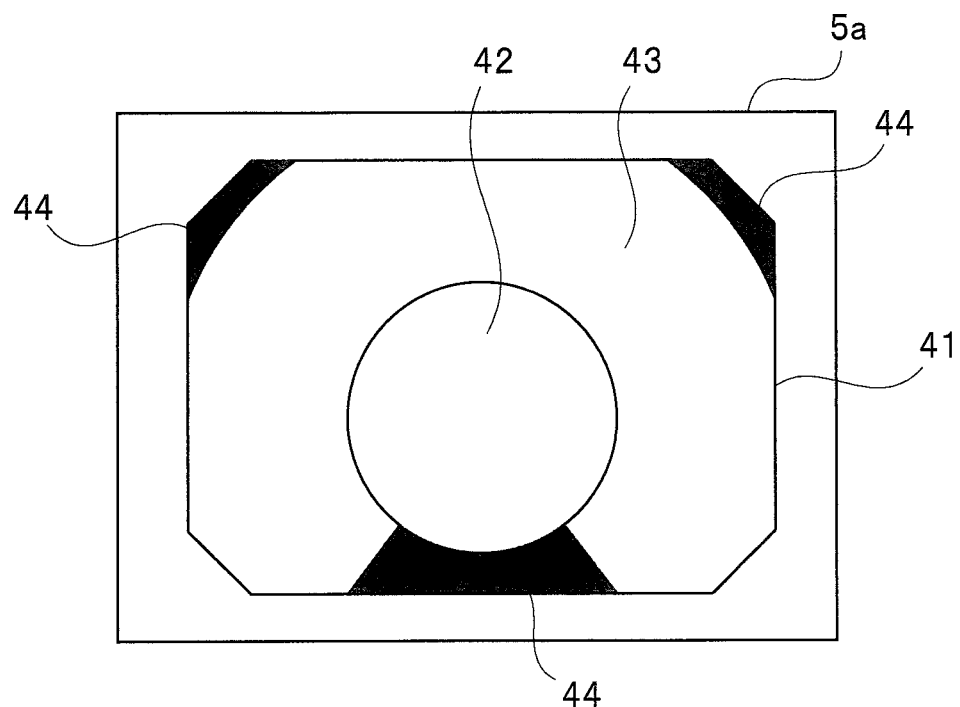
FIG. 5 is a view showing an example of an observed image displayed on a monitor as a display apparatus by image processing performed by a video processor of the endoscope system according to the first embodiment of the present invention.

FIG. 1 is a configuration diagram showing a configuration of an endoscope system according to the present embodiment. FIG. 2 is a perspective view showing a configuration of a distal end portion of an insertion portion of an endoscope. FIG. 3 is a front view showing the configuration of the distal end portion of the insertion portion of the endoscope. FIG. 4 is a sectional view of a distal end portion 6a along an axial direction of an insertion portion 6. FIG. 5 is a view showing an example of an observed image displayed on a monitor as a display apparatus by image processing performed by a video processor of the endoscope system.

An endoscope system 1 includes an endoscope 2, a processor 3 being a video processor, and a light source apparatus 4. A monitor 5 which is a display apparatus is connected to the processor 3. The endoscope 2 picks up an image of an observation target (object) and outputs an image pickup signal. The processor 3 generates and outputs a video signal in accordance with the image pickup signal. The light source apparatus 4 supplies illumination light for illuminating an observation target. The monitor 5 displays an observed image being an endoscope image in accordance with the video signal.

The endoscope 2 includes an insertion portion 6 having flexibility and configured to be inserted inside a subject, and an operation portion (not shown) connected to a proximal end of the insertion portion 6. The endoscope 2 is connected to the processor 3 and the light source apparatus 4 by using a universal code 2a.

The insertion portion 6 configured to be inserted inside the subject includes a hard distal end portion 6a provided on the most distal end side, a bendable bending portion 6b provided at a rear end of the distal end portion 6a, and a long flexible tube portion 6c having flexibility and provided at a rear end of the bending portion 6b.

The distal end portion 6a of the insertion portion 6 is provided with two front illumination windows 7 and one front observation window 8 for a front visual field, and two side illumination windows 9 and one side observation window 10 for a side visual field.

In addition, a light guide 11 made of an optical fiber bundle is used for illumination. Illumination light for the two front illumination windows 7 and the two side illumination windows 9 is incident on a proximal end portion of the light guide 11. The distal end portion of the light guide 11 is divided into four sections, and the respective sections are disposed on rear sides of the two front illumination windows 7 and the two side illumination windows 9 so that the illumination light is emitted from each of the windows.

The bending portion 6b is provided on a proximal end side of the distal end portion 6a of the insertion portion 6 having flexibility. The bending portion 6b has a bending mechanism (not shown) built inside, such as a mechanism with a plurality of bending pieces continuously provided so as to be bendable in vertical and horizontal directions, or a mechanism, so-called swinging mechanism, rotatable around a predetermined axis so as to be able to change a direction of an optical axis of the image acquisition portion.

A bending nob as a bending operation portion is provided in the operation portion, not shown. By operating the bending nob, a plurality of bending wires connected to the bending mechanism are pulled or loosened, so that the user can bend the bending portion 6b in a desired direction such as the vertical or horizontal direction.

The endoscope 2 of the present embodiment is a wide-angle endoscope configured to display a plurality of visual field images so as to make a visual field of 180 degrees or more observable, and achieves prevention of oversight in a place which is hard to view only by front observation, such as the back of layers and a boundary of organs in a body cavity, especially the large intestine.

As shown in FIG. 2, in the distal end portion 6a of the insertion portion 6, a columnar cylindrical portion 12 is formed, which is provided protruding from a position located above the center of the distal end surface of the distal end portion 6a.

A distal end portion of the cylindrical portion 12 is provided with an objective optical system, described later, for observation in both the front visual field and the side visual field. The front observation window 8 is disposed in a place corresponding to the front of the objective optical system in the distal end portion of the cylindrical portion 12. The side observation window 10 is disposed in a place corresponding to a side visual direction of the objective optical system in the distal end portion of the cylindrical portion 12.

Further, in vicinities of the distal end surface of the cylindrical portion 12 and a proximal end portion of the cylindrical portion 12, the front illumination window 7 configured to emit light for illuminating the front is provided. In the proximal end portion of the cylindrical portion 12, the two side illumination portions 9 configured to emit light for illuminating the sides are provided. The side observation window 10 being an image acquisition portion is disposed closer to the proximal end portion of the cylindrical portion 12 than the front observation window 8 being the image acquisition portion.

FIG. 4 shows a cross section of the distal end portion 6a having been cut off so that cross sections of the side illumination window 9, the front illumination window 7, the front observation window 8, and the side observation window 10 can be seen.

On a rear side of the front illumination window 7, a distal end surface of a part of the light guide 11 is set up. The front observation window 8 is provided on a distal end surface of a distal end hard member 31. An objective optical system 32 is set up on a rear side of the front observation window 8.

An image pickup unit 33 is set up on a rear side of the objective optical system 32. Note that a cover 31a is attached to a distal end portion of the distal end hard member 31. In addition, the insertion portion 6 is covered with an envelope 31b.

Hence illumination light for the front is emitted from the front illumination window 7 and reflected light from an object being an observed region in the subject is incident on the front observation window 8.

The two side illumination windows 9 are set up on a side surface of the distal end hard member 31, and the distal end surface of a part of the light guide 11 is set up on the rear of each side illumination window 9 via a mirror 34 with the reflection surface being a curved surface.

Therefore, the two front illumination windows 7 and the two side illumination windows 9 constitute an illumination light emitting section configured to emit, inside the subject, first illumination light to an area including the front as a first area and second illumination light to an area including the sides as a second area which is different from the first area.

The side observation window 10 is set up on the side surface of the distal end hard member 31, and the objective optical system 32 is set up on a rear side of the side observation window 10. Hence the objective optical system 32 is configured so as to turn, toward the image pickup unit 33, reflected light passing through the front observation window 8 and coming from the front and reflected light having passed through the side observation window 10 and coming from the side. In FIG. 4, the objective optical system 32 includes two optical members 35, 36. The optical member 35 is a lens having a convex surface 35a, and the optical member 36 has a reflection surface 36a configured to reflect light from the convex surface 35a of the optical member 35 toward the image pickup unit 33 via the optical member 35.

An image pickup surface of the image pickup device 33a of the image pickup unit 33 is disposed in an image formation position of the objective optical system 32, such that an image of the observation target in the visual field of the front observation window 8 is formed at a center as a circular front visual field image, and that an image of the observation target in the visual field of the side observation window 10 is formed on an outer periphery part of the front visual field image as an annular side visual field image.

That is, the front observation window 8 is provided on the distal end surface of the distal end portion 6a of the insertion portion 6 and constitutes a first image acquisition portion (first object image acquisition portion, first subject image acquisition portion) configured to acquire a first image (a first object image, a first subject image) from a first area which is an area including the front of the insertion portion, and the side observation window 10 is provided on the distal end surface of the distal end portion 6a of the insertion portion 6 and constitutes a second image acquisition portion (second object image acquisition portion, second subject image acquisition portion) configured to acquire a second image (second object image, second subject image) from a second area which is an area different from the first area and including the side of the insertion portion.

More specifically, the first image is an object image in a first direction (a subject image in the first direction) including the front of the insertion portion 6 which is substantially parallel to a longitudinal direction of the insertion portion 6, and the second image is an object image in a second direction (a subject image in the second direction) including the side of the insertion portion 6 which is substantially orthogonal to the longitudinal direction of the insertion portion 6.

The second area being different from the first area means that an optical axis in the area is oriented differently from an optical axis in the first area. The first object image and the second object image may or may not partially overlap, and further, a range of irradiation with the first illumination light and a range of irradiation with the second illumination light may or may not partially overlap.

The front observation window 8 being the image acquisition portion is disposed in the distal end portion 6a of the insertion portion 6 in a direction in which the insertion portion 6 is inserted, and the side observation window 10 being the image acquisition portion is disposed in a side surface portion of the insertion portion 6 in an outer diameter direction of the insertion portion 6. The image pickup unit 33 being an image pickup section is disposed so as to photoelectrically convert an object image from the front observation window 8 and an object image from the side observation window 10 on the same image pickup surface and is electrically connected to the processor 3.

That is, the front observation window 8 is a front image acquisition portion (front object image acquisition portion, front subject image acquisition portion) disposed on the distal end surface of the distal end portion 6a of the insertion portion 6 such that the first object image is acquired from the direction in which the insertion portion 6 is inserted, and the side observation window 10 is a side image acquisition portion (side object image acquisition portion, side subject image acquisition portion) disposed along the peripheral direction of the distal end portion 6a of the insertion portion 6 such that the second object image is acquired from the second direction. The image pickup unit 33 electrically connected to the processor 3 includes one image pickup device 33a and receives the first object image and the second object image on one image pickup surface to photoelectrically convert the images and supply image pickup signals to the processor 3.

Therefore, illumination light for the front is emitted from the front illumination window 7 and reflected light from the object is incident on the image pickup unit 33 through the front observation window 8, while illumination light for the side is emitted from the two side illumination windows 9 and reflected light from the object is incident on the image pickup unit 33 through the side observation window 10. The image pickup device 33a of the image pickup unit 33 photoelectrically converts the optical image of the object and outputs an image pickup signal to the processor 3.

As above, the endoscope 2 includes: a front observation optical system configured to form an optical image of a front area; a side observation optical system configured to form an optical image of a side area; and an image pickup device configured to pick up an optical image of the front area and an optical image of the side area.

FIG. 5 shows an example of the observed image being the endoscope image displayed on the monitor 5. An observed image 41 being an endoscope image displayed on the display screen 5a of the monitor 5 is a substantially rectangular image and has two areas 42, 43. The circular area 42 at the center is an area displaying the front visual field image, and the C-shaped area 43 around the area 42 provided at the center is an area displaying the side visual field image.

That is, the front visual field image is an image obtained via the front illumination window 7 and displayed on the display screen 5a of the monitor 5 so as to be formed in a substantially circular shape, and the side visual field image is an image obtained via the side illumination window 9 and displayed on the display screen 5a so as to be formed in a substantially annular shape surrounding at least a part of around the front visual field image. With the side visual field image formed in the annular shape so as to surround the circular front visual field and disposed adjacent to the front visual field image, the front visual field image and the side visual field image are displayed on the monitor 5 being the display apparatus. A wide-angle endoscope image is displayed on the monitor 5.

The observed image shown in FIG. 5 is generated from the acquired images acquired by the image pickup device 33a (FIG. 4). The observed image 41 is generated such that the object image projected on the image pickup surface of the image pickup device 33a by the objective optical system provided in the distal end portion 6a is photoelectrically converted and the image portion of the front visual field at the center which corresponds to the area 42 and the image portion of the side visual field which corresponds to the area 43, excluding a mask area 44 painted in black and synthesized.

Returning to FIG. 2, the distal end surface of the distal end portion 6a is provided with a distant end opening portion 37 which is communicated with a treatment instrument channel, not shown and disposed in a position adjacent to the cylindrical portion 12, and enables protrusion of a distal end portion of a treatment instrument inserted in the treatment instrument channel.

Further, the distal end portion 6a of the insertion portion 6 includes a support portion 38 provided so as to protrude from the distal end surface of distal end portion 6a, and the support portion 38 is located adjacent to a lower side of the cylindrical portion 12.

The support portion 38 is configured so as to be able to support or hold each of protruding members that are disposed so as to protrude from the distal end surface of the distal end portion 6a. Specifically, the support portion 38 is configured so as to be able to support or hold a front observation window nozzle portion 39 configured to inject air or liquid for cleaning the front observation window 8, the front illumination window 7 configured to emit light for illuminating the front direction, and a side observation window nozzle portion 40 configured to inject air or liquid for cleaning the side observation window 13, as the respective protruding members described above.

In the meantime, the support portion 38 is formed including a shielding portion 38a which is an optical shielding member for preventing acquisition of such a side visual field image as including any of the respective protruding members described above which are bodies different from an original observation target, due to appearance of each of the protruding members in the side visual field. That is, by providing the shielding portion 38a in the support portion 38, it is possible to obtain such a side visual field image as including none of the front observation window nozzle portion 39, the front illumination window 7, and the side observation window nozzle portion 40.

As shown in FIGS. 2 and 3, the side observation window nozzle portion 40 is provided at two places in the support portion 38 and disposed such that the distal end protrudes from a side surface of the support portion 38.

Returning to FIG. 1, the processor 3 is an image processing apparatus for endoscope which includes a control section 21, an image generation section 22, an image processing section 23, an image pickup unit driving section 24, a setting input section 25, and an image recording section 26.

The control section 21 includes a central processing unit (CPU), a ROM, a RAM, and the like, and controls a whole endoscope system. The ROM stores a plurality of programs in accordance with various functions.

The image generation section 22 generates a display signal for an observed image being an endoscope image that is displayed on the monitor 5 from an image obtained based on an image pickup signal from the image pickup unit 33 under control of the control section 21.

Especially, the image generation section 22 performs generation of an observed image obtained based on an image pickup signal outputted from the image pickup unit 33 under control of the control section 21, and performs other operations. The front visual field image and the side visual field image are generated by being cut out from the observed image obtained by the image pickup device 33a.

That is, the image generation section 22 generates the first image and the second image obtained respectively from the first area of the object at the front of the insertion portion which is substantially parallel to the longitudinal direction of the insertion portion 6 of the endoscope 2 and the second area of the object on the side of the insertion portion which intersects with the longitudinal direction of the insertion portion 6.

The image processing section 23 executes enhancement processing, described later, on the display signal for the observed image.

The image pickup unit driving section 24 is connected to the image pickup unit 33 through a signal line, not shown. The image pickup unit driving section 24 drives the image pickup unit 33 under control of the control section 21. The driven image pickup unit 33 generates an image pickup signal and supplies the generated signal to the image generation section 22.

The setting input section 25 is an input apparatus including various operation equipment such as a keyboard, a button, a mouse, and a touch pad, and used by the user to input a setting, an operation instruction, and the like related to each of various functions of the endoscope system 1 into the processor 3. Note that the setting input section 25 may include analog operation equipment capable of continuously changing a value, such as a dial or a knob.

The control section 21 sets and inputs, into each processing section such as the image processing section 23, the setting information and the operation instruction information inputted in the setting input section 25. The setting information includes a parameter for the enhancement processing described later, and the parameter is inputted or set in the setting input section 25.

The image recording section 26 is a recording section configured to record the observed images generated in the image generation section 22 and the image processing section 23 under control of the control section 21, and includes a non-volatile memory such as a hard disk drive.

The observed image recorded by the image recording section 26 can be selected or specified by the setting. The user may specify, for example, whether to record the observed image generated in the image generation section 22 and whether to record the observed image subjected to the enhancement processing in the image processing section 23. The user can specify from the setting input section 25 an observed image to be recorded by the image recording section 26. That is, the image recording section 26 can record an image including the front visual field image subjected to the image enhancement processing and the side visual field image subjected to the image enhancement processing.

The light source apparatus 4 is a light source apparatus having a lamp for emitting white light built inside, and configured to emit illumination light into the distal end of the light guide 11 and to control on-off and an amount of the illumination light under control of the control section 21. The control section 21 controls the light source apparatus 4 to perform exposure control on the observed image.

(Configuration of Image Enhancement Processing of Image Processing Section)

Figure 6:
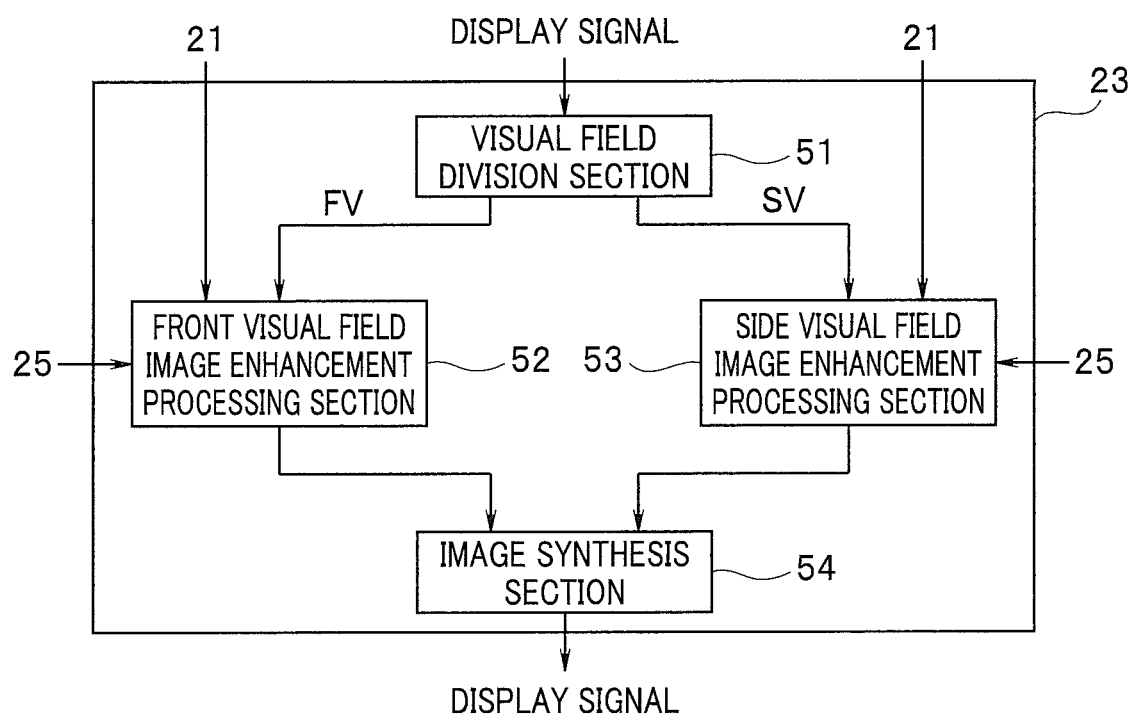
FIG. 6 is a block diagram of image enhancement processing that is executed in an image processing section 23 according to the first embodiment of the present invention.

FIG. 6 is a block diagram of the image enhancement processing that is executed in the image processing section 23.

The image processing section 23 executes various types of image processing including the image enhancement processing. FIG. 6 only shows a processing block concerning the image enhancement processing in the image processing section 23. The image processing section 23 includes a visual field division section 51, a front visual field image enhancement processing section 52, a side visual field image enhancement processing section 53, and an image synthesis section 54.

As described above, the image generation section 22 generates a display signal for an observed image being an endoscope image under control of the control section 21, and supplies the image processing section 23 with the generated display signal.

The display signal from the image generation section 22 is inputted into the visual field division section 51 and divided into an image signal for an image in the area 42 described above, namely a front visual field image FV, and an image signal for an image in the area 43 described above, namely a side visual field image SV.

The visual field division section 51 outputs to the front visual field image enhancement processing section 52 the image signal for the front visual field image FV extracted by dividing the display signal, and outputs to the side visual field image enhancement processing section 53 the image signal for the side visual field image SV extracted by dividing the display signal. The visual field division section 51 constitutes a separation section configured to separate between the front image and the side image from image pickup signals outputted from the image pickup device.

The front visual field image enhancement processing section 52 and the side visual field image enhancement processing section 53 respectively execute previously set image enhancement processing on the front visual field image FV and the side visual field image SV. The front visual field image enhancement processing section 52 and the side visual field image enhancement processing section 53 can both execute a plurality of types of image enhancement processing and execute specified image enhancement processing. The plurality of types of image enhancement processing include structure enhancement, contour enhancement, and hue enhancement processes. The structure enhancement processing is processing of enhancing contrast of an image or a rate of change in color tone. The contour enhancement processing is processing of thickly enhancing a portion with the contrast or change in color tone of the image. The hue enhancement processing is processing of enhancing hue of the image.

The user can input and set, from the setting input section 25, a parameter for the image enhancement processing of each of the front visual field image enhancement processing section 52 and the side visual field image enhancement processing section 53 and can change the set parameter value. The user can individually set parameters for the front visual field image enhancement processing section 52 and the side visual field image enhancement processing section 53, and each image enhancement processing is executed in each of the front visual field image enhancement processing section 52 and the side visual field image enhancement processing section 53 based on the set parameter, for example, an enhancement level.

The parameters include a type of enhancement processing in each observation scene, and an enhancement level for each image enhancement processing in each observation scene. That is, for each of the front visual field image FV and the side visual field image SV, the parameters include type information of the image enhancement processing (e.g., any of the structure enhancement, the contour enhancement, and the hue enhancement) used in each observation scene and level information of the enhancement level of the enhancement processing used in each scene. Therefore, the image processing section 23 can change the image enhancement processing on the front visual field image FV and the image enhancement processing on the side visual field image SV in accordance with the observation scene in examination with the endoscope 2. The image enhancement processing on the front visual field image FV and the image enhancement processing on the side visual field image SV may be different types of image enhancement processing in each observation scene.

Note that, when only one type of image enhancement processing is used, the parameter only includes the enhancement level of the image enhancement processing to be used in each scene.

The image enhancement processing in each of the front visual field image enhancement processing section 52 and the side visual field image enhancement processing section 53 is executed based on the control signal from the control section 21.

The image signal for the front visual field image FV and the image signal for the side visual field image SV subjected to the image enhancement processing respectively in the front visual field image enhancement processing section 52 and the side visual field image enhancement processing section 53 are supplied to the image synthesis section 54.

As above, the image processing section 23 individually adjusts the enhancement level of the image enhancement processing that is performed on the front visual field image FV and the enhancement level of the image enhancement processing that is performed on the side visual field image SV disposed adjacent to the front visual field image FV, to perform the image enhancement processing on the front visual field image FV and the image enhancement processing on the side visual field image SV.

The image synthesis section 54 synthesizes the front visual field image FV and the side visual field image SV, each subjected to the image enhancement processing to generate a display signal and output the generated signal to the monitor 5.

In accordance with an observation scene specified by the operator, the control section 21 supplies each of the front visual field image enhancement processing section 52 and the side visual field image enhancement processing section 53 with the control signal for executing the image enhancement processing in accordance with the observation scene. The operator can specify the observation scene by operating a predetermined button or the like in the setting input section 25.

Hence the monitor 5 displays observed images obtained by individually performing the image enhancement processing on the front visual field image FV and the side visual field image SV in accordance with the observation scene.

Note that in the example described above, the enhancement processing is performed differently on each of the front visual field image FV and the side visual field image SV extracted by dividing the display signal, but the set image enhancement processing may be performed on each area in the display signal for one observed image without dividing the display signal. For example, the enhancement processing set for the front visual field image FV may be performed on a pixel belonging to the area 42 in the display signal and the enhancement processing set for the side visual field image SV may be performed on a pixel belonging to the area 43 in the display signal. In this case, the image synthesis section 54 is unnecessary.

(Action)

Next, enhancement processing in accordance with a specific observation scene will be described.

Figure 7:
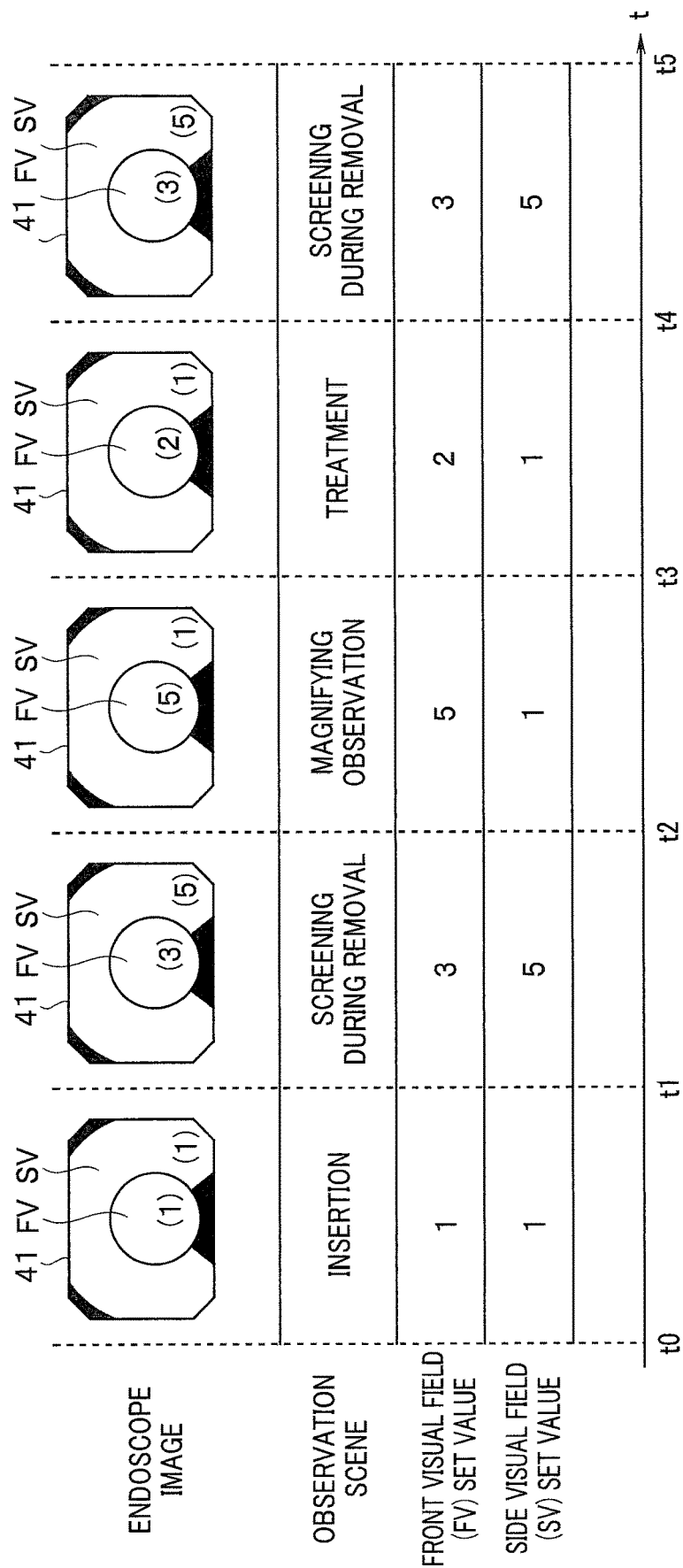
FIG. 7 is a diagram showing changes in set values of image enhancement processing parameters in accordance with observation scenes according to the first embodiment of the present invention.

FIG. 7 is a diagram showing changes in set values of image enhancement processing parameters in accordance with observation scenes. A horizontal axis indicates the lapse of time. The parameter for the enhancement level of the image enhancement processing in each scene according to each of the front visual field image FV and the side visual field image SV shown in FIG. 7 is previously stored into each of the front visual field image enhancement processing section 52 and the side visual field image enhancement processing section 53. A number in parentheses in each area in the observed image 41 on the upper row of FIG. 7 shows a set enhancement level described later.

Note that an example will be described where one set image enhancement processing is performed on each of the front visual field image FV and the side visual field image SV and the enhancement level is set as the parameter, but when the type of image enhancement processing that is executed varies in each observation scene, the type of the enhancement processing in each scene and the enhancement level of the enhancement processing are set as parameters.

Note that the enhancement level will be described using an example where "1", the lowest degree of image enhancement, to "5", the highest degree of image enhancement, are settable, but the enhancement levels may include "0" at which the image enhancement processing is not performed.

First, for example in the case of conducting examination by inserting the insertion portion 6 of the endoscope 2 into a lumen such as the large intestine, the operator inserts the insertion portion 6 into the farthest section of the lumen, and hence the observation scene is an insertion scene.

As described above, the operator can specify a current observation scene by pressing a predetermined button in the setting input section 25 as an observation scene specification section. The operator thus selects an observation scene of "insertion." FIG. 7 shows that the observation scene of the "insertion" was specified by the operator at a time t0.

As shown in FIG. 7, when the observation scene is "insertion", the same "1" is set in each of the front visual field image FV and the side visual field image SV as the enhancement level of the image enhancement. This is because, if noise in a deep dark portion of the lumen is conspicuous at the time of inserting the insertion portion 6, the noise gives the operator stress, and hence the enhancement level of the image enhancement of the front visual field image is set low so as to make the image enhancement on the front visual field image FV low.

Further, at the time of inserting the insertion portion 6, a bending direction of the lumen in a curved portion or the like may be determined by using the side visual field image SV, and hence the enhancement level of the image enhancement on the side visual field image SV is set low similarly to the front visual field image FV.

Next, when the insertion portion 6 is inserted into the farthest section of the lumen, the operator performs screening for finding the presence or absence of a lesion by looking at a lumen wall while removing the insertion portion 6, so that the operator changes the observation scene to an observation scene of "screening during removal", namely, a screening scene, and the observation scene thus becomes a scene at the time of screening while removing the insertion portion 6. FIG. 7 shows that the observation scene of the "screening during removal" was specified by the operator at a time t1.

When the observation scene is the "screening during removal", "3" and "5" are set as the enhancement levels of the image enhancement respectively in the front visual field image FV and the side visual field image SV. This is because, at the time of screening, the side visual field image SV is used for finding a lesion, and the enhancement level of the image enhancement on the side visual field image SV is thus set high to make the image enhancement on the side visual field image SV strong so as to prevent oversight in a lesion.

If noise in the image is conspicuous, the noise gives the operator stress, and hence the image enhancement is not made strong so as to reduce tiredness of the operator. However, at the time of screening during removal, if the enhancement is excessively weak, the lesion found in the side visual field image SV is hard to visually recognize. Therefore, a certain degree of enhancement is required and the enhancement level of the image enhancement on the front visual field image FV is thus set at a medium degree.

As above, when the observation scene is the "screening during removal", the enhancement level of the side visual field image SV is higher than the enhancement level of the front visual field image FV so that the image enhancement in the image enhancement processing on the side visual field image SV is stronger than the image enhancement in the image enhancement processing on the front visual field image FV. That is, when the observation scene is the screening scene, the control section 21 individually sets the enhancement level by the front image enhancement processing section and the enhancement level by the side image enhancement processing section so as to make an amount of enhancement on the side image relatively larger than an amount of enhancement on the front image.

When a lesion is found in the "screening during removal", the operator selects an observation scene of "magnifying observation", namely, a magnifying scene, in order to magnify and observe the lesion, and the observation scene thus becomes the magnifying observation scene. FIG. 7 shows that the observation scene of the "magnifying observation" was specified by the operator at a time t2.

When the observation scene is the "magnifying observation", "5" and "1" are set as the enhancement levels of the image enhancement respectively in the front visual field image FV and the side visual field image SV. This is because, due to the operator using the front visual field image FV to perform the magnifying observation on the lesion, the enhancement level of the image enhancement on the side visual field image is set low so as to weaken the enhancement on the front visual field image FV and reduce noise of the side visual field image SV.

Further, at the time of the magnifying observation, the operator wishes to firmly recognize and diagnose a structure of the blood vessel even when noise in the image in the front visual field image FV increases, and hence the enhancement level of the enhancement processing on the front visual field image FV is set high.

As a result of the magnifying observation, the operator may wish to perform treatment on the lesion. In that case, the operator changes the observation scene to an observation scene of "treatment", namely, a treatment scene, and the observation scene thus becomes the treatment scene. FIG. 7 shows that the observation scene of the "treatment" was specified by the operator at a time t3.

When the observation scene is the "treatment", "2" and "1" are set as the enhancement levels of the image enhancement respectively in the front visual field image FV and the side visual field image SV. This is because, with the front visual field image FV mainly used also in the treatment, the enhancement level of the enhancement processing on the side visual field image is set low so as to weaken the enhancement on the front visual field image FV for reduction in noise of the side visual field image SV.

At the time of treatment, only the size of the lesion may have to be recognizable while the structure of the blood vessel is not recognizable, whereby the enhancement level of the enhancement processing on the front visual field image FV is set lower than the enhancement level at the time of the magnifying observation and the screening so as to reduce the noise in the image.

As above, when the observation scene is the magnifying scene or the treatment scene, the control section 21 sets the enhancement level by the front image enhancement processing section and the enhancement level by the side image enhancement processing section so as to make an amount of enhancement on the front image relatively larger than an amount of enhancement on the side image.

Then, the control section 21 sets the enhancement level by the front image enhancement processing section such that the amount of enhancement on the front image at the time of the observation scene being the treatment scene is relatively smaller than the amount of enhancement on the front image at the time of the observation scene being the magnifying scene.

After the treatment, the operator further performs screening for finding the presence or absence of a lesion by looking at the lumen wall while removing the insertion portion 6, so that the operator selects the observation scene of the "screening during removal", and the observation scene thus becomes the scene at the time of screening while removing the insertion portion 6. FIG. 7 shows that the observation scene of the "screening during removal" was specified by the operator at a time t4.

The enhancement levels which are set as parameters with the levels of enhancement respectively on the front visual field image FV and the side visual field image SV are the same as the values in the observation scene of the "screening during removal" described above. FIG. 7 shows that the observation scene of the "screening during removal" was ended at a time t5.

Figure 8:
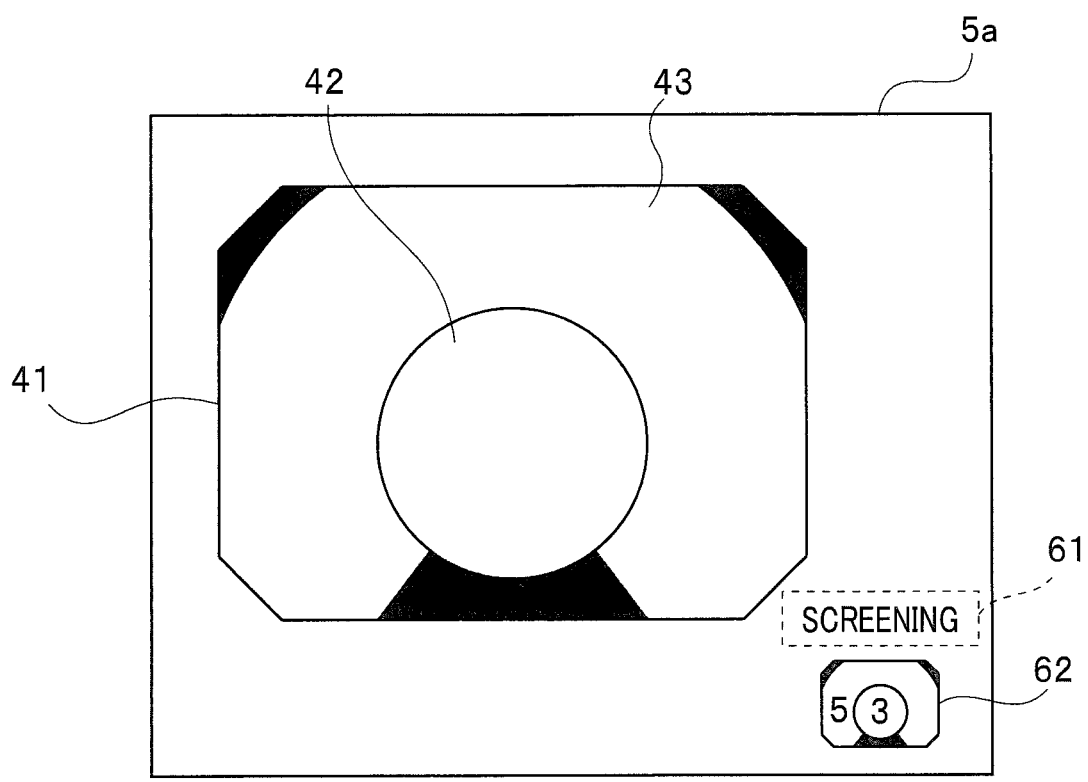
FIG. 8 is a view showing a display example of a display screen that is displayed during endoscopy according to the first embodiment of the present invention.

FIG. 8 is a view showing a display example of a display screen that is displayed during endoscopy.

As shown in FIG. 8, on the display screen 5a of the monitor 5, the image processing section 23 displays the observed image 41 including the front visual field image FV and the side visual field image SV subjected to the image enhancement, and generates and displays an information display portion displaying information of the observation scene and information of the enhancement levels of the respective areas 42, 43 in the observed image 41.

Specifically, in the display screen 5a, a scene information display portion 61 indicating the current observation scene and a level information display portion 62 indicating the enhancement levels of the respective areas 42, 43 in the observed image 41. That is, the information representing the observation scene is added to the front image having passed through the front image enhancement processing section and the side image having passed through the side image enhancement processing section and is outputted to the monitor 5 being the display apparatus. In FIG. 8, characters "Screening" are displayed as the observation scene in the scene information display portion 61, and the operator can confirm that the current observation scene for the processor 3 is the scene of the "screening during removal."

Further, in the level information display portion 62, along with a figure being a patterned shape of the observed image 41, a number "3" is displayed in an area of a figure corresponding to the area 42 of the front visual field image and a number "5" is displayed in an area of a figure corresponding to the area 43 of the side visual field image SV. The operator can recognize that the observed image 41 is displayed in which the enhancement processing has been performed with the enhancement level of the area 42 of the front visual field image FV set to "3" and the enhancement level of the area 43 of the side visual field image set to "5." That is, information representing the enhancement level of the enhancement processing is added to each of the front image having passed through the front image enhancement processing section and the side image having passed through the side image enhancement processing section and is outputted to the monitor 5 being the display apparatus.

Moreover, the operator can also recognize that the displayed enhancement levels are also set as the observation scene of the "screening during removal."

Especially in the level information display portion 62, the enhancement levels of the respective areas 42, 43 in the observed image 41 are displayed, so that the operator can confirm the enhancement levels of the respective areas 42, 43 when the observation scene is changed.

As above, the image processing section 23 causes the level information display portion and the scene information display portion to be displayed on the monitor 5 being the display apparatus configured to display the front visual field image FV and the side visual field image SV, the level information display portion displaying the enhancement level of the front visual field image FV and the enhancement level of the side visual field image SV, the scene information display portion displaying the observation scene in examination with the endoscope 2.

Note that in the case of recording the observed image 41 as an examination result, the image recording section 26 may store, into a non-volatile memory such as a hard disk drive, both original data of the observed image 41, namely, image data of an observed image not subjected to the image enhancement, and image data of an observed image subjected to the image enhancement. However, along with the original data of the observed image 41 not subjected to the image enhancement, data of the parameter (the type and enhancement level of the image enhancement processing) of each of the areas 42, 43 in the recorded observed image 41 may be stored into the non-volatile memory such as the hard disk drive in temporal association with the original data of the observed image 41.

In that case, at the time of reproducing the recorded observed image 41, it is possible to generate the observed image 41 subjected to the image enhancement at the time of recording, from the original image data of the recorded observed image 41 so as to reproduce and display the generated image on the monitor 5.

As above according to the embodiment described above, it is possible to provide an endoscope system capable of performing image enhancement processing on a plurality of visual field images each having a different role in each observation scene, the processing being suited for each role.

Next, modifications will be described.
(Modification 1)

Although one enhancement level is set in each of the front visual field image FV and the side visual field image SV in the embodiment described above, one of or both the front visual field image FV and the side visual field image SV may be divided into a plurality of areas and an enhancement level may be set in each of the divided areas.

Figure 9:
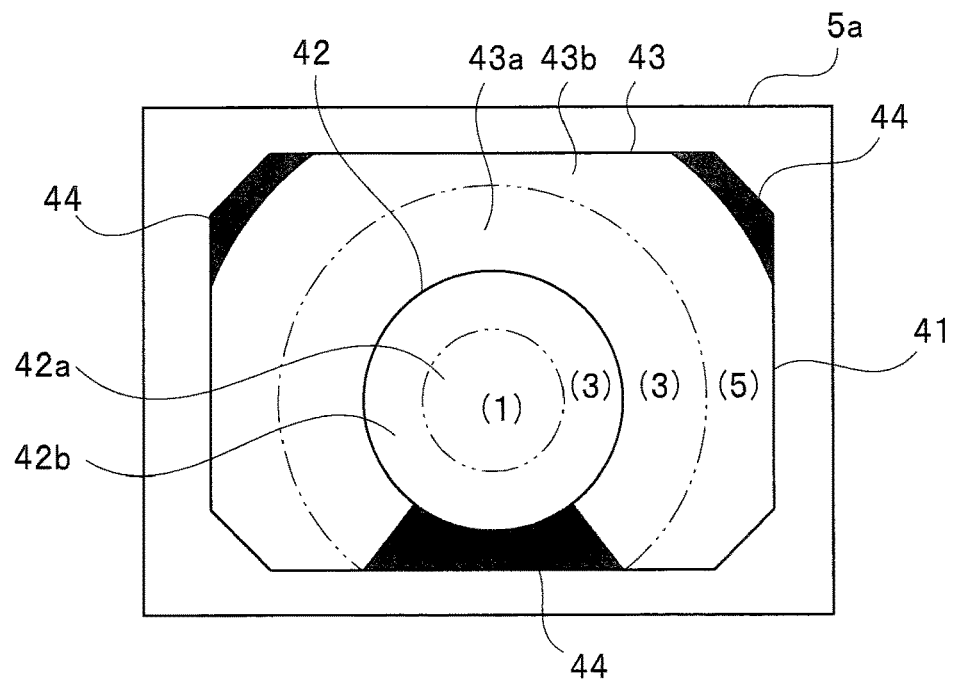
FIG. 9 is a view showing an example of an observed image obtained by dividing each of a front visual field image FV and a side visual field image SV into a plurality of areas according to Modification 1 of the first embodiment of the present invention.

FIG. 9 is a view showing an example of an observed image obtained by dividing each of the front visual field image FV and the side visual field image SV into a plurality of areas according to Modification 1.

As indicated in a two-dot chain line in FIG. 9, the area 42 of the front visual field image FV is further divided into two areas, a circular area 42a at the center and an annular area 42b around the area 42a. Further, the area 43 of the side visual field image SV is divided into two areas, an annular area 43a on a central side and an annular area 43b around the area 43a. In the visual field division section 51 or the front visual field image enhancement processing section 52 and the side visual field image enhancement processing section 53 described above, the front visual field image FV and the side visual field image SV are each divided into a plurality of areas, here, two areas.

An enhancement parameter in accordance with each scene in each divided area is inputted from the setting input section 25 and set and recorded in each of the front visual field image enhancement processing section 52 and the side visual field image enhancement processing section 53. Hence at least one of the enhancement levels of the front visual field image FV and the enhancement level of the side visual field image SV is different in each of the areas of the front visual field image FV and the side visual field image SV from the other.

When the scene is selected or specified, the control section 21 supplies scene information of the specified observation scene to the front visual field image enhancement processing section 52 and the side visual field image enhancement processing section 53, and the front visual field image enhancement processing section 52 and the side visual field image enhancement processing section 53 execute the image enhancement processing on the respective areas by using a parameter in accordance with the observation scene, selected based on the supplied scene information.

In FIG. 9, as indicated by numbers in parentheses, the area 42a at the center in the area 42 of the front visual field image FV is set to the lowest enhancement level value ("1" in FIG. 9"), and the peripheral area 42b in the area 42 of the front visual field image FV is set to the middle-degree enhancement level ("3" in FIG. 9).

In the side visual field image SV, the area 43a close to the front visual field image FV is set to a value of the middle-degree enhancement level ("3" in FIG. 9). In the side visual field image SV, the area 43b distant from the front visual field image FV is set to a value of the high enhancement level ("5" in FIG. 9). That is, each enhancement level in the side visual field image SV is set such that the image enhancement is stronger as distance from the front visual field image FV increases. The enhancement level in the side visual field image SV is the highest in a position most distant from the front visual field image FV.

Further, as shown in FIG. 9, the enhancement levels of the two areas close to each other in the two adjacent images are set to the same value. This is intended so that, for example, when a lesion or the like moves from the side visual field image SV to the front visual field image FV, the appearance of the lesion does not look discontinuous.

Further, with the wide-angle endoscope, it is possible to observe an area only viewable from a deep side of the lumen when a view angle is wide, such as the back of layers of the intestinal wall, and when an area in the side visual field image SV which is the farthest from the front visual field image FV is set at the highest enhancement level, a lesion on the back of the layers or the like can be displayed with image enhancement at the highest enhancement level, so that oversight in the lesion can be prevented.

That is, maximizing the enhancement level of the outer periphery part of the annular side visual field image SV facilitates finding of the lesion on the back of the layers or the like.

Note that in FIG. 9, the area 42 of the front visual field image FV and the area 43 of the side visual field image SV are each divided into two areas, but may be divided into three areas or more.

(Modification 2)

As Modification 2, the enhancement level of one of or both the front visual field image FV and the side visual field image SV may be set in accordance with a position of each pixel.

Figure 10:
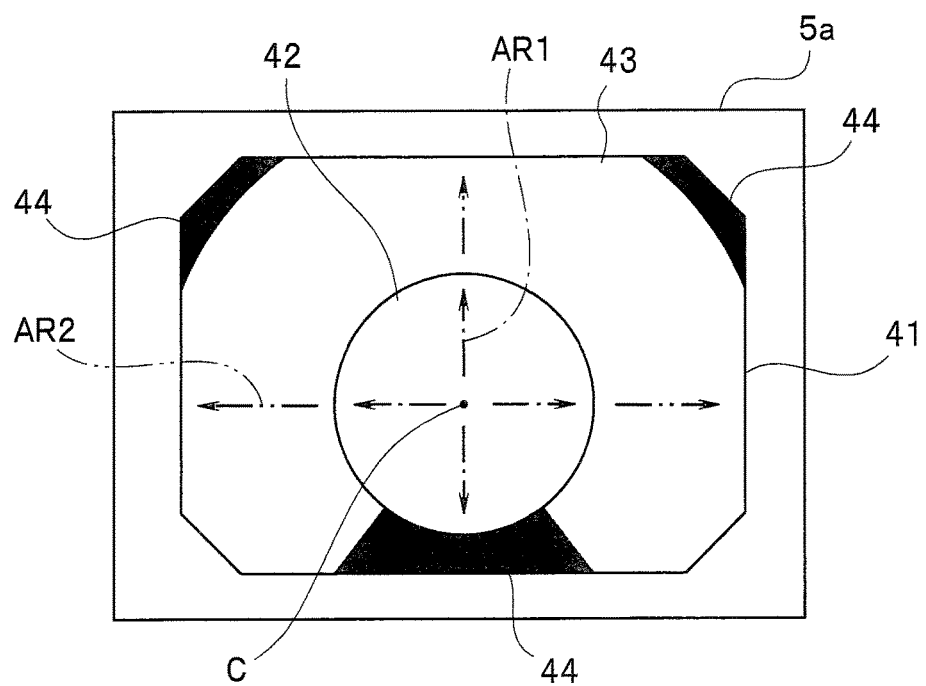
FIG. 10 is a view for describing a setting of an enhancement level that changes in accordance with a position of each pixel in each of the front visual field image FV and the side visual field image SV according to Modification 2 of the first embodiment of the present invention.

FIG. 10 is a view for describing a setting of the enhancement level that changes in accordance with the position of each pixel in each of the front visual field image FV and the side visual field image SV.

As shown in FIG. 10, at each pixel in the area 42 of the front visual field image FV, the enhancement level is set in accordance with a distance from a center C of the circle. For example, the enhancement level for each pixel in the area 42 of the front visual field image FV is set such that the enhancement level gradually increases from the center C toward a periphery part along a direction shown by an arrow AR1 indicated by a one-dot chain line. Moreover, in order to strengthen the image enhancement of the side visual field image SV as distance from the front visual field image FV increases, the enhancement level for each pixel in the area 43 of the side visual field image SV is set such that the enhancement level gradually increases from an inner periphery part to an outer periphery part of an annulus ring of the area 43 along a direction shown by an arrow AR2 indicated by a two-dot chain line. That is, the enhancement level of the side visual field image SV continuously varies in accordance with a distance from the front visual field image FV. The enhancement level in the side visual field image SV is the highest in a position most distant from the front visual field image FV.

Especially by matching or substantially matching the enhancement level of the outer periphery part of the front visual field image FV with the enhancement level of the inner periphery part of the side visual field image SV, the enhancement levels of the front visual field image FV and the side visual field image SV continuously vary, whereby it is possible to eliminate an unnatural feeling at the time of viewing the front visual field image FV and the side visual field image SV.

Note that, although the enhancement level is set in accordance with the position of each pixel in both the front visual field image FV and the side visual field image SV in FIG. 10, for example, one enhancement level may be set as a whole in the front visual field image FV and the enhancement level may be set so as to gradually increase from the inner periphery part toward the periphery part only in the side visual field image SV.

(Modification 3)

Although the enhancement level of each area is previously set for each observation scene in the embodiment and each of Modifications 1 and 2 described above, the previously set enhancement level may be made changeable during observation.

For example, when the display screen 5a as in FIG. 8 or FIG. 9 is displayed on the monitor 5, upon specification of a desired area, the operator may be able to change an enhancement level of the specified area to a desired level. It is possible to specify an area in which an enhancement level is to be changed and to change the enhancement level, by using the mouse or the like in the setting input section 25. For example, when the operator specifies the area 42 of the front visual field image FV with the mouse or the like and inputs a value with a keyboard, only the enhancement level of the area 42 is changed while the enhancement level of the area 43 of the side visual field image SV is not changed.

When the previously set enhancement level is changeable during observation, the operator can perform determination on the condition of the lesion, and the like, from more pieces of information.

(Modification 4)

Although the enhancement processing is performed on the previously set area in the embodiment described above, the enhancement processing may be performed only on a desired area in each area.

Figure 11:
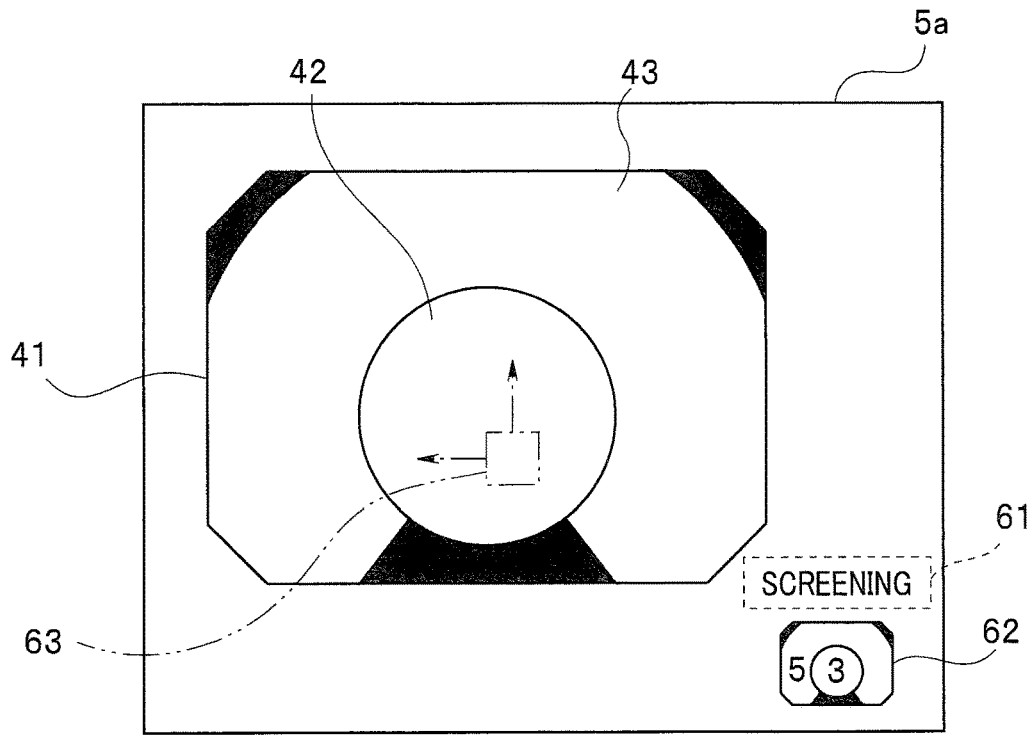
FIG. 11 is a view showing a display example of a display screen 5a that is displayed during examination according to Modification 4 of the first embodiment of the present invention.

FIG. 11 is a view showing a display example of the display screen 5a that is displayed during examination according to Modification 4. For example, in FIG. 11, a frame 63 indicated by a two-dot chain line is displayed under instruction of the user, and the user can move the frame 63 in a freely selectable direction as indicated by the arrow in accordance with an instruction from the setting input section 25. Then, an image with the image enhancement processing performed only in the area on the frame 63 may be displayed, and an image with the image enhancement processing not performed on an area other than the frame 63 may be displayed.

The operator can specify an area to be subjected to the image enhancement processing in a freely selectable manner and can thus observe only a desired area in more detail to find a lesion or perform determination on a state of the lesion, or the like.

Note that each area may be previously divided into a plurality of areas, and in accordance with an instruction of the user, an area to be subjected to the image enhancement processing may be made changeable among the plurality of divided areas.

Figure 12:
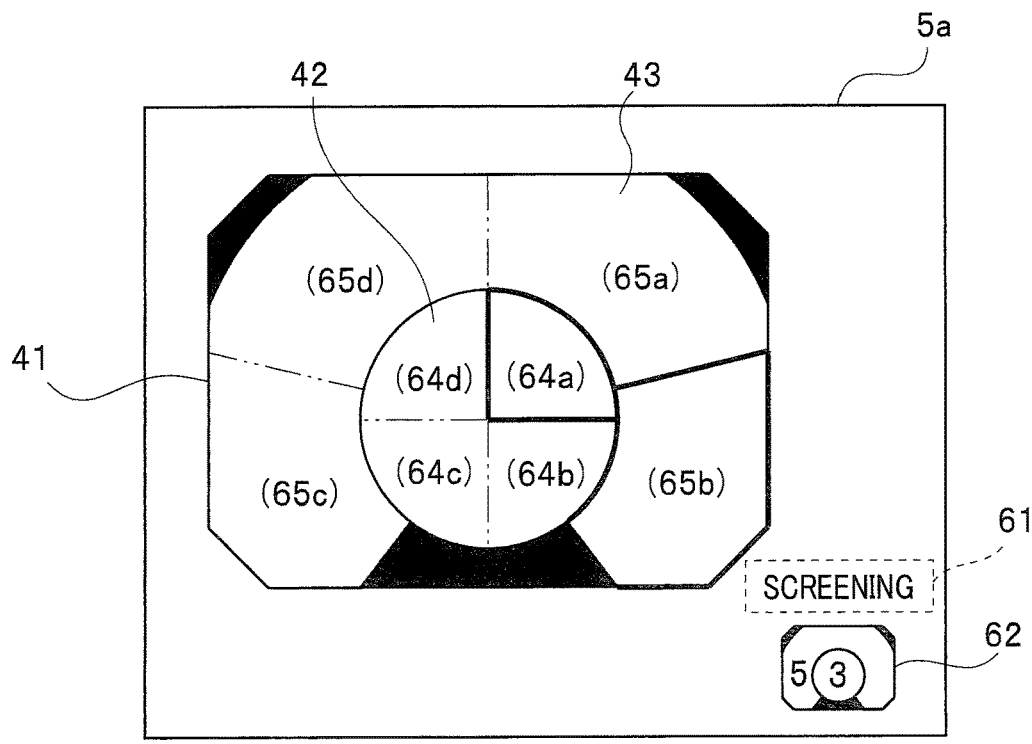
FIG. 12 is a view showing the other display example of the display screen 5a that is displayed during examination according to Modification 4 of the first embodiment of the present invention.

FIG. 12 is a view showing the other display example of the display screen 5a that is displayed during examination according to Modification 4. For example, in FIG. 12, the front visual field image FV is previously divided into four areas 64a, 64b, 64c, 64d, and the side visual field image SV is also previously divided into four areas 65a, 65b, 65c, 65d. When the user selects any of the areas 42, 43 to be subjected to the image enhancement processing by using the mouse or the like in the setting input section 25 and selects and specifies any of the areas 64a, 64b, 64c, 64d or the areas 65a, 65b, 65c, 65d by using a predetermined button or the like in the setting input section 25, an image with only the specified areas subjected to the image enhancement processing is displayed.

In FIG. 12, the selected area is indicated by a thick frame, and the operator can see that the areas 64a, 65b subjected to the enhancement processing have been selected. In the areas other than the areas 64a, 65b, an image not subjected to the enhancement processing is displayed.

Also by the screen display as in FIG. 12, the operator can observe only the desired area in more detail to find a lesion or perform determination on the state of the lesion, or the like.

As above, according to the first embodiment and each of Modifications 1 to 4 described above, it is possible to provide an endoscope system capable of performing image enhancement processing on a plurality of visual field images each having a different role, the processing being suited for each role.

Second Embodiment

While the endoscope system 1 of the first embodiment uses the endoscope 2 that obtains a front visual field image and a side visual field image disposed so as to surround the front visual field image with one image pickup device, an endoscope system 1A of a second embodiment uses an endoscope 2A that obtains a front visual field image and a side visual field image with separate image pickup devices.

Note that in a configuration of the endoscope system 1A of the second embodiment, the same components as the components in the endoscope system 1 described in the first embodiment are provided with the same numerals and description of the components are omitted.

(Configuration)

Figure 13:
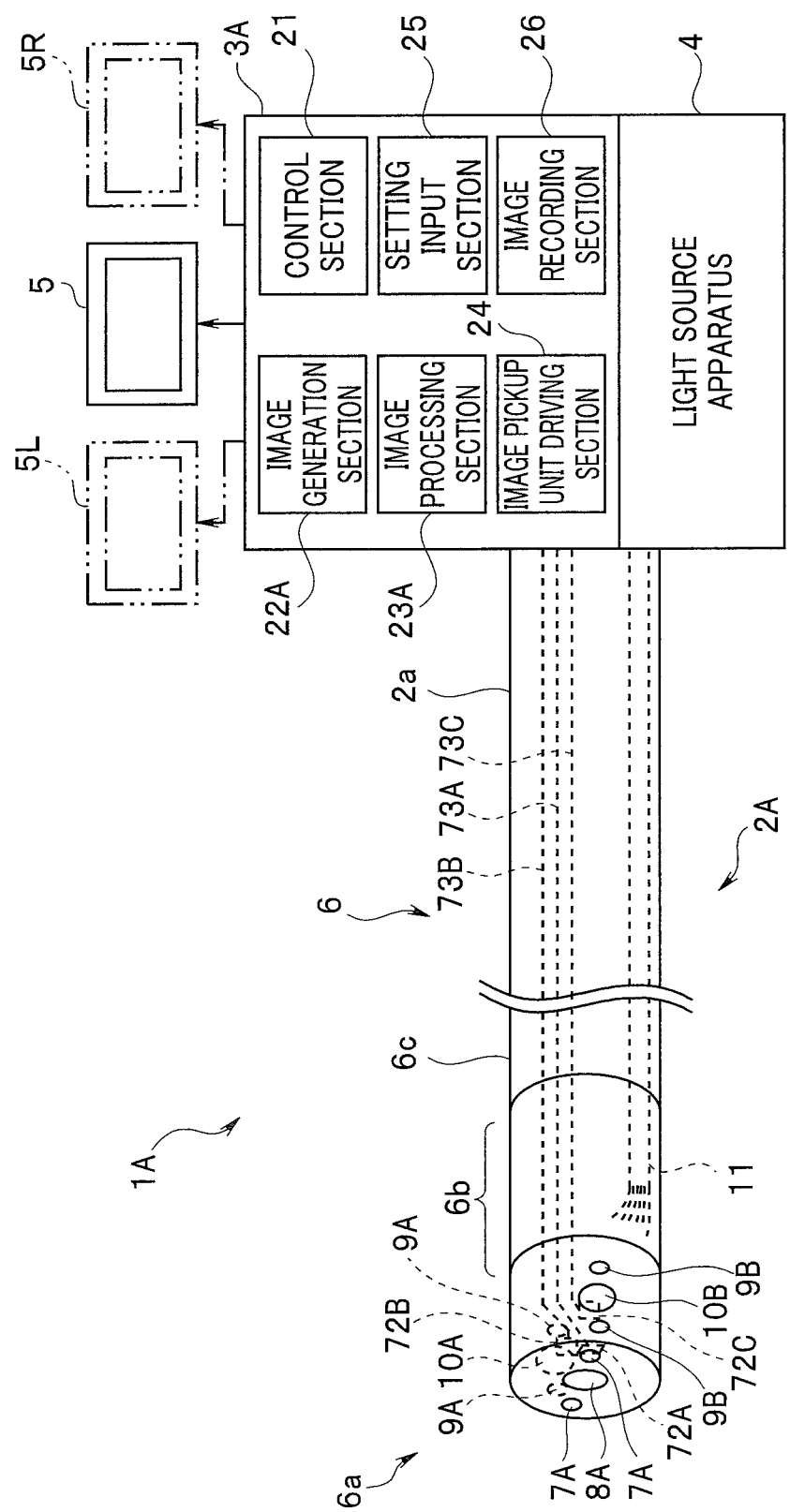
FIG. 13 is a block diagram showing a configuration of an endoscope system according to a second embodiment of the present invention.
Figure 14:
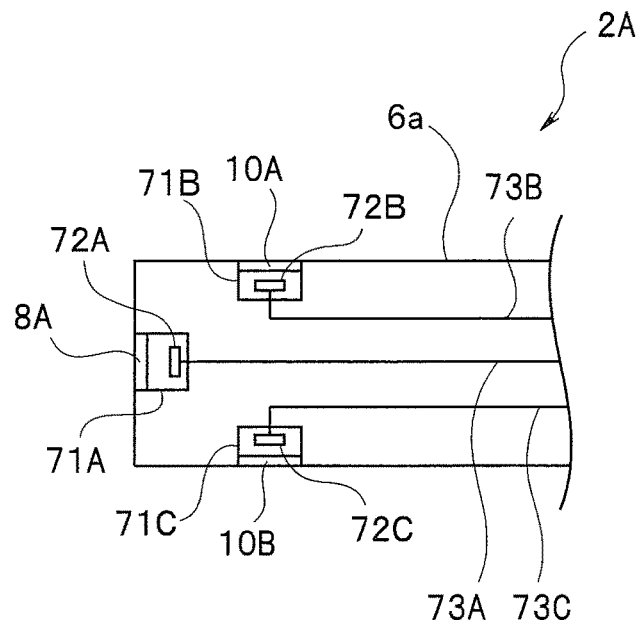
FIG. 14 is a schematic sectional view showing a configuration of a distal end portion 6a of an endoscope 2A according to the second embodiment of the present invention.

FIG. 13 is a block diagram showing the configuration of the endoscope system according to the present embodiment. FIG. 14 is a schematic sectional view showing a configuration of a distal end portion 6a of the endoscope 2A in the present embodiment. Note that in FIG. 13, only components related to the function of the present embodiment described below, and components related to the other functions are omitted.

As shown in FIG. 13, the endoscope system 1A includes the endoscope 2A, a processor 3A being a video processor, a light source apparatus 4, and a monitor 5.

A description will be given of the configuration of the distal end portion 6a of the insertion portion 6 that is inserted inside a subject in the endoscope 2A. As shown in FIG. 14, an image pickup unit 71A for front visual field is provided inside a distal end surface of columnar distal end portion 6a of the endoscope 2A. Two image pickup units 71B, 71C for side visual field are provided inside a side surface of the distal end portion 6a of the endoscope 2A. The three image pickup units 71A, 71B, 71C respectively include image pickup devices 72A, 72B, 72C, and an objective optical system, not shown, is provided in each image pickup unit.

The image pickup units 71A, 71B, 71C are respectively disposed on rear surface sides of a front observation window 8A and the two side observation windows 10A, 10B. The respective image pickup units 71A, 71B, 71C receive reflected light from an object being an observed region in the subject, illuminated by illumination light emitted from a plurality of illumination windows 7A, 9A, 9B provided in the distal end portion 6a which respectively correspond to the image pickup units 71A, 71B, 71C, and output image pickup signals.

Three image pickup signals from the three image pickup devices 72A, 72B, 72C are inputted into an image generation section 22A via signal lines 73A, 73B, 73C, respectively.

The front observation window 8A is disposed in a direction in which the insertion portion 6 is inserted on the distal end portion 6a of the insertion portion 6. The side observation windows 10A, 10B are disposed in a side surface portion of the insertion portion 6 in a direction of an outer diameter of the insertion portion 6 at an angle substantially equivalent to a peripheral direction of the distal end portion 6a, and the side observation windows 10A, 10B are disposed in directions opposite to each other in the distal end portion 6a.

The image pickup devices 72A, 72B, 72C of the image pickup units 71A, 71B, 71C are electrically connected to a processor 3A and output image pickup signals to the processor 3A as controlled by the processor 3A. Each of the image pickup units 71A, 71B, 71C is an image pickup section configured to photoelectrically convert an object image.

The front observation window 8A is provided on the distal end surface of the distal end portion 6a of the insertion portion 6 and constitutes a first image acquisition portion (first object image acquisition portion, first subject image acquisition portion) configured to acquire a first object image (first image, first subject image) from a first area including a direction being a first direction in which the insertion portion 6 is inserted (the front). In other words, the front observation window 8A is the front image acquisition portion (front object image acquisition portion, front subject image acquisition portion) configured to acquire an object image in the area including the front of the insertion portion 6, and a first object image is an object image (subject image) obtained via the front observation window 8A and located in an area including the front of the insertion portion, substantially parallel to the longitudinal direction of the insertion portion 6.

Each of the side observation windows 10A, 10B is provided in the distal end portion 6a in the longitudinal direction of the insertion portion 6, and constitutes a second image acquisition portion (second object image acquisition portion, second subject image acquisition portion) configured to acquire a second object image (second image, second subject image) from a second area including the side of the insertion portion 6 which is a second direction different from the first direction. In other words, each of the side observation windows 10A, 10B is the side image acquisition portion (side object image acquisition portion, side subject image acquisition portion) configured to acquire an object image in the area including a direction intersecting with the longitudinal direction of the insertion portion 6 at such an angle as a regular angle, and second object images are two object images (subject images) obtained via the side observation windows 10A, 10B and located in areas including the side of the insertion portion in the direction intersecting with the longitudinal direction of the insertion portion 6.

As above, the endoscope 2A includes: a front observation optical system configured to form an optical image of the front area; a side observation optical system configured to form an optical image of the side area; an image pickup device configured to pick up an optical image of the front area and generate the front image; and an image pickup device formed as a separate body from the above image pickup device and configured to pick up an optical image of the side area and generate a side image.

The image pickup unit 71A is an image pickup section configured to photoelectrically convert an image from the front observation window 8A, and the image pickup units 71B, 71C are image pickup sections configured to photoelectrically convert two images from the side observation windows 10A, 10B, respectively. That is, the image pickup unit 71A is an image pickup section configured to pick up an object image for acquiring a front visual field image, and the image pickup units 71B, 71C are image pickup sections configured to pick up object images for acquiring side visual field images, respectively. An image signal for the front visual field image, which is the first visual field image serving as a main image and displayed all the time, is generated from the image obtained in the image pickup unit 71A, and image signal for the side visual field images, which are the second visual field images serving as sub-images and changing a display form as necessary, are generated from images obtained in the image pickup units 71B, 71C.

Although not shown, end portions branched from the light guide 11 are set up on rear sides of the respective illumination windows 7A, 9A, 9B.

The image generation section 22A generates the front visual field image FV and the side visual field image SV obtained respectively from the first area of the object in front the insertion portion which is substantially parallel to the longitudinal direction of the insertion portion 6 of the endoscope 2, and the second area of the object in side of the insertion portion which intersects with the longitudinal direction of the insertion portion 6.

Specifically, the image generation section 22A of the processor 3A in the endoscope system 1A inputs image pickup signals from the three image pickup devices 72A, 72B, 72C of the three image pickup units 71A, 71B, 71C to generate observed images, which are endoscope images, from the respective image pickup signals. That is, the front visual field image FV is generated from the image pickup signal of the image pickup device 72A, a right-hand side visual field image SV is generated from the image pickup signal of the image pickup device 72B, and a left-hand side visual field image SV is generated from the image pickup signal of the image pickup device 72C.

The image processing section 23A inputs three display signals from the image generation section 22A to execute predetermined enhancement processing. Similarly to the image processing section 23 of the first embodiment, the image processing section 23A individually adjusts the enhancement level of the image enhancement processing that is performed on the front visual field image FV and the enhancement level of the image enhancement processing that is performed on each side visual field image SV disposed adjacent to the front visual field image FV, to perform the image enhancement processing on the front visual field image FV and the image enhancement processing on each side visual field image SV.

Figure 15:
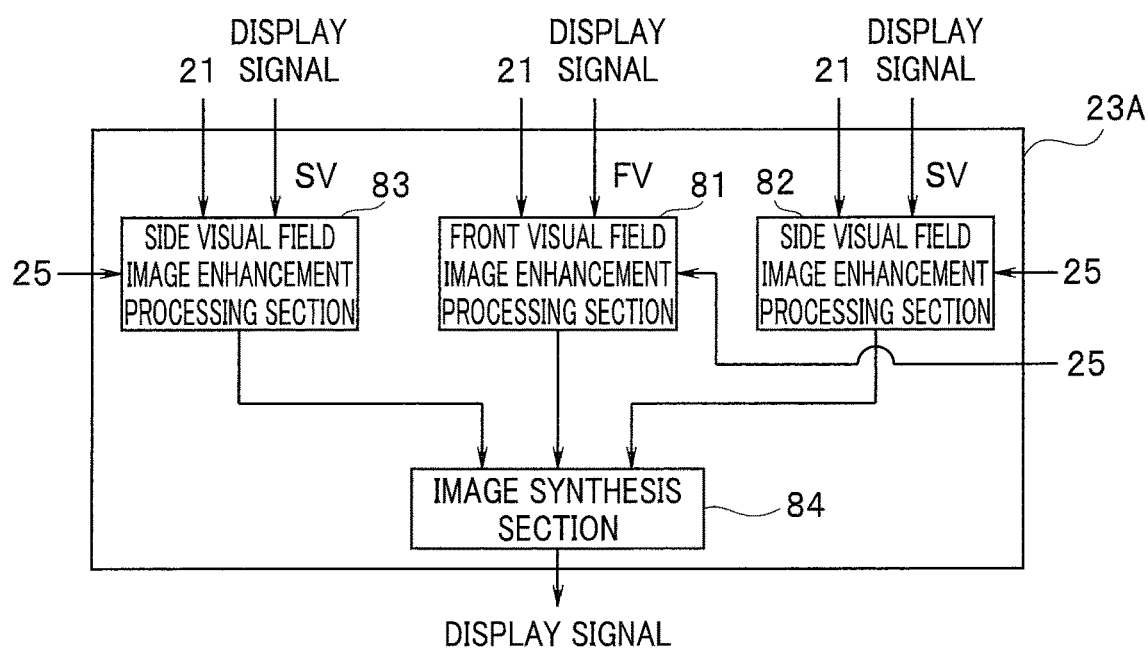
FIG. 15 is a block diagram of image enhancement processing that is executed in an image processing section 23A according to the second embodiment of the present invention.

FIG. 15 is a block diagram of the image enhancement processing that is executed in the image processing section 23A.

The image processing section 23A executes various types of image processing including the enhancement processing. FIG. 15 only shows a processing block according to the image enhancement processing in the image processing section 23A.

The image generation section 22A generates display signals for three observed images under control of the control section 21, and the three generated display signals are supplied to the image processing section 23A.

The three display signals from the image generation section 22A are inputted into the corresponding image enhancement processing sections. The image signal for the front visual field image FV is inputted into the front visual field image enhancement processing section 81, the image signal for the right-hand side visual field image SV is inputted into the side visual field image enhancement processing section 82, and the image signal for the left-hand side visual field image SV is inputted into the side visual field image enhancement processing section 83.

The front visual field image enhancement processing section 81 and the side visual field image enhancement processing sections 82, 83 respectively execute previously set image enhancement processing on the front visual field image FV and the right-hand and left-hand side visual field images SV. Also, in the present embodiment, any of the front visual field image enhancement processing section 81 and the side visual field image enhancement processing sections 82, 83 can execute a plurality of types of image enhancement processing. The plurality of types of image enhancement processing include structure enhancement, contour enhancement, and hue enhancement.

The user can change, from the setting input section 25, a setting of a parameter for the image enhancement processing on each of the front visual field image enhancement processing section 81 and the two side visual field image enhancement processing sections 82, 83. The parameters set by the user are set in the front visual field image enhancement processing section 81 and the side visual field image enhancement processing sections 82, 83, and each image enhancement processing is executed based on the set parameter data, for example, an enhancement level.

Similarly to the first embodiment, the parameters include a type of image enhancement processing in each observation scene, and an enhancement level for each image enhancement processing. That is, for each of the front visual field image FV and the two side visual field images SV, the parameters includes type information of the image enhancement processing (e.g., any of the structure enhancement, the contour enhancement, and the hue enhancement) used in each observation scene, and level information of the enhancement level of the enhancement processing used in each scene. Therefore, the image processing section 23 can change the image enhancement processing on the front visual field image FV and the image enhancement processing on each of side visual field image SV in accordance with the observation scene in examination with the endoscope 2. Then, the image enhancement processing on the front visual field image FV and the image enhancement processing on each of side visual field images SV can be made to vary from one another in each observation scene.

Note that, when only one type of image enhancement processing is used, the parameter only includes the enhancement level of the image enhancement processing to be used in each observation scene.

The image enhancement processing in each of the front visual field image enhancement processing section 81 and the side visual field image enhancement processing sections 82, 83 is executed based on the control signal from the control section 21.

The respective image signals for the front visual field image FV and the two side visual field images SV subjected to the image enhancement processing in the front visual field image enhancement processing section 81 and the two side visual field image enhancement processing sections 82, 83 are supplied to the image synthesis section 84.

The image synthesis section 84 synthesizes the front visual field image FV and the two side visual field images SV to generate a display signal and output the generated signal to the monitor 5.

Figure 16:
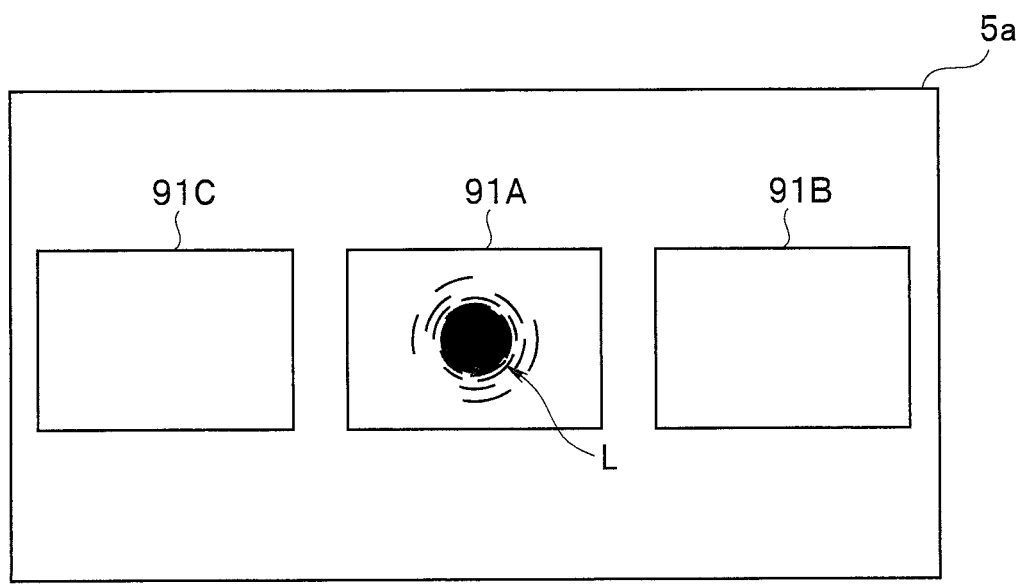
FIG. 16 is a view showing an example of an observed image displayed on a display screen 5a of a monitor 5 according to the second embodiment of the present invention.

FIG. 16 is a view showing an example of the observed image displayed on the display screen 5a of the monitor 5. As shown in FIG. 16, the front visual field image FV is displayed in an area 91A at the center in the display screen 5a of the monitor 5. A first side visual field image SV being the right-hand side visual field image is displayed in a right-hand area 91B in the display screen 5a of the monitor 5. A second side visual field image SV being the left-hand side visual field image is displayed in a left-hand area 91C in the display screen 5a of the monitor 5. In FIG. 16, an image at the time of the user performing examination by inserting the insertion portion into the large intestine is displayed, and a lumen L is displayed in the front visual field image FV. With the two side visual field images SV displayed on both sides of the front visual field image FV, a wide-angle endoscope image is displayed on the monitor 5.

That is, the front visual field image FV and the side visual field images SV are disposed adjacent to each other such that the two side visual field images SV sandwich the front visual field image FV, and the front visual field image FV and the two side visual field images SV are displayed on the monitor 5 being the display apparatus.

Note that, although three images are displayed in the display screen 5a of one monitor 5, the respective images may be displayed on individual monitors. For example, in FIG. 13, two monitors 5R, 5L may be provided in addition to the monitor 5 as indicated by two-dot chain lines, the front visual field image FV may be displayed on the monitor 5, the first side visual field image SV being the right-hand side visual field image may be displayed on the monitor 5R, and the second side visual field image SV being the left-hand side visual field image may be displayed on the monitor 5L. In this case, the image synthesis section 84 is unnecessary.
(Action)

Next, enhancement processing in accordance with a specific examination scene in the present embodiment will be described.

Figure 17:
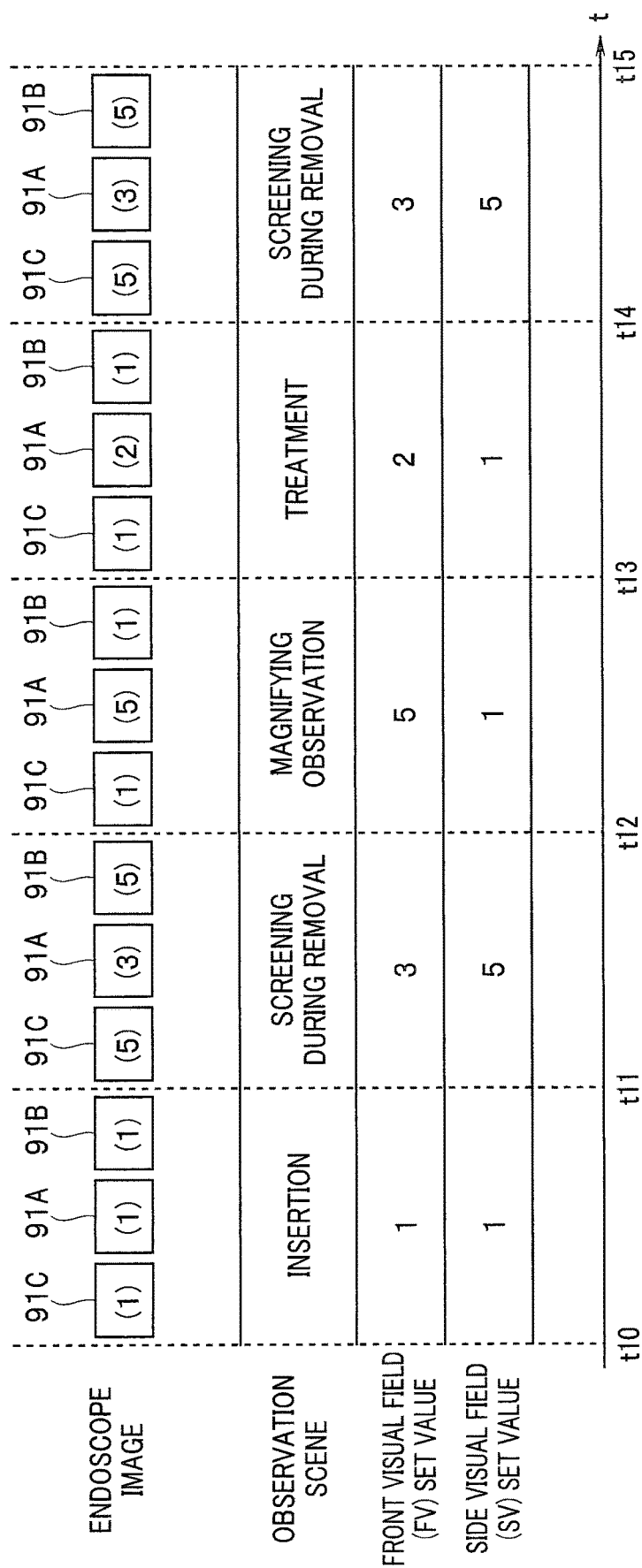
FIG. 17 is a diagram showing changes in set values of enhancement processing parameters in accordance with observation scenes according to the second embodiment of the present invention.

FIG. 17 is a diagram showing changes in set values of enhancement processing parameters in accordance with observation scenes. A horizontal axis indicates the lapse of time. The parameter for the enhancement level of the image enhancement processing in each scene according to each of the front visual field image FV and the two side visual field images SV shown in FIG. 17 is previously stored into each of the front visual field image enhancement processing section 81 and the side visual field image enhancement processing sections 82, 83. A number in parentheses in each area in the observed image on the upper row of FIG. 17 shows a set enhancement level described later.

Note that, similarly to the first embodiment, the enhancement level will be described again using an example where "1", the lowest degree of image enhancement, to "5", the highest degree of image enhancement, are settable, but the enhancement levels may include "0" at which the image enhancement processing is not performed.

FIG. 17 gives a description with the same observation scenes as in FIG. 7 taken as examples. A period from a time t10 to a time t11 corresponds to the period for the observation scene of the "insertion" from the time t0 to the time t1 in FIG. 7, a period from the time t11 to a time t12 corresponds to the period for the observation scene of the "screening during removal" from the time t1 to the time t2 in FIG. 7, a period from the time t12 to a time t13 corresponds to the period for the observation scene of the "magnifying observation" from the time t2 to the time t3 in FIG. 7, a period from the time t13 to a time t14 corresponds to the period for the observation scene of the "treatment" from the time t3 to the time t4 in FIG. 7, and a period from the time t14 to a time t15 corresponds to the period for the observation scene of the "screening during removal" from the time t4 to the time t5 in FIG. 7.

Figure 18:
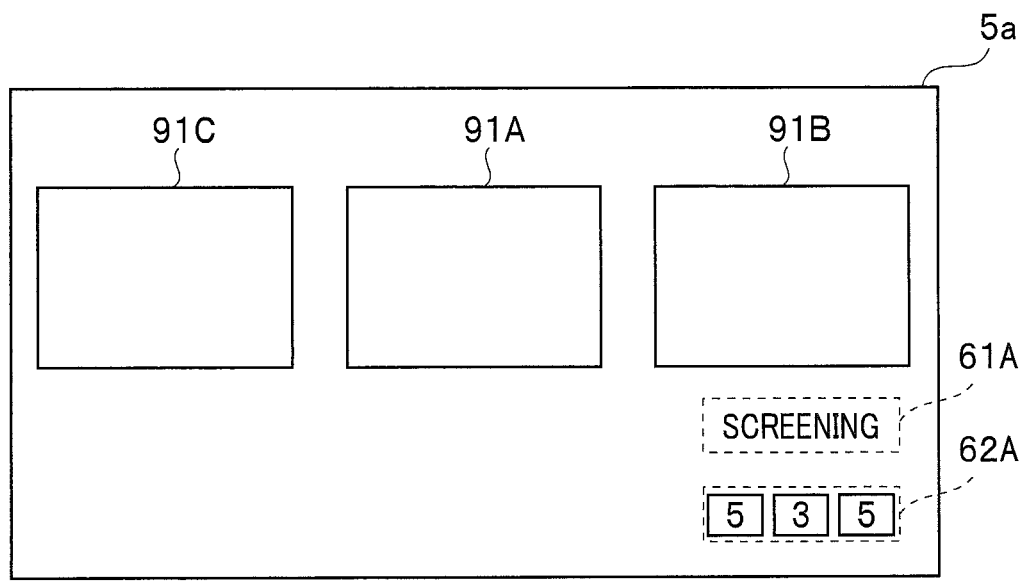
FIG. 18 is a view showing a display example of a display screen that is displayed during endoscopy according to the second embodiment of the present invention.

FIG. 18 is a view showing a display example of a display screen that is displayed during endoscopy.

As shown in FIG. 18, on the display screen 5a of the monitor 5, the image processing section 23A displays an image including the front visual field image FV and the two side visual field images SV subjected to the image enhancement, and displays an information display portion displaying information of the observation scene and information of the enhancement level of each area in the observed image.

Specifically, in the display screen 5a, a scene information display portion 61A indicating the current observation scene and a level information display portion 62A indicating the enhancement levels of the respective areas 91A, 91B, 91C in the observed image. In FIG. 18, characters "Screening" are displayed as the observation scene in the scene information display portion 61A, and the operator can confirm that the current observation scene for the processor 3A is the "screening during removal."

Further, in the level information display portion 62A, along with figures being patterned shapes and placement of the three observed images, a number "3" is displayed in an area of the figure corresponding to the area 91A of the front visual field image, and a number "5" is displayed in each of the areas of the figures corresponding to the areas 91B, 91C of the right-hand and left-hand side visual field images. The operator can recognize that the three endoscope images as observed images are displayed by performing the image enhancement processing with the enhancement level of the area 91A of the front visual field image set to "3" and the enhancement levels of the areas 91B, 91C of the side visual field images set to "5."

The level information display portion 62A provides a similar effect to the effect of the level information display portion 62 of the first embodiment.

As above, according to the embodiment described above, it is possible to provide an endoscope system capable of performing image enhancement processing on a plurality of visual field images each having a different role in each observation scene, the processing being suited for each role.

Note that in the present embodiment, depending on the necessity of the observation scene such as detailed observation of a portion included in a predetermined side visual field, it may be possible to perform image enhancement processing with a different level on each of the right-hand and left-hand side visual field images SV, such as image enhancement processing with the enhancement level of the right-hand side visual field image set to "5" and the enhancement level of the left-hand side visual field image set to "3."

Next, Modifications 5 to 9 of the second embodiment will be described.
(Modification 5)

Although one enhancement level is set in each of the front visual field image FV and the two side visual field images SV in the embodiment described above, any one, any two, or all of the front visual field image FV and the two side visual field images SV may be divided into a plurality of areas and an enhancement level may be set in each of the divided areas.

Figure 19:
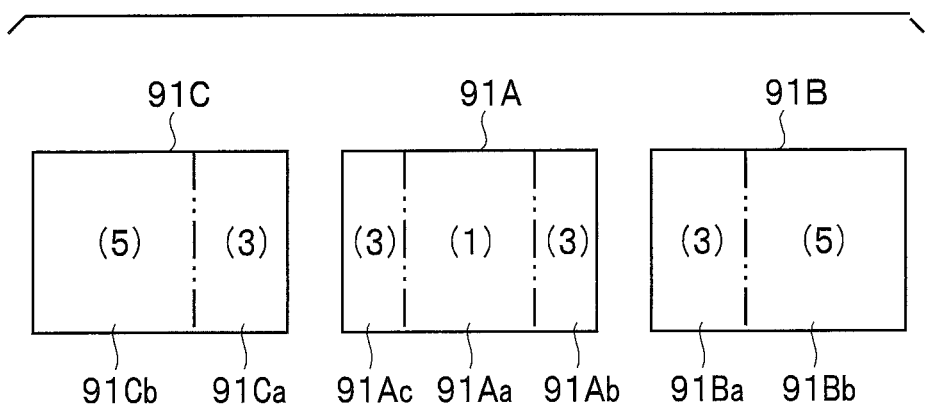
FIG. 19 is a view showing an example of observed images obtained by dividing each of a front visual field image FV and two side visual field images SV into a plurality of areas according to Modification 5 of the second embodiment of the present invention.

FIG. 19 is a view showing an example of observed images obtained by dividing each of the front visual field image FV and the two side visual field images SV into a plurality of areas according to Modification 5.

In FIG. 19, as indicated by two-dot chain lines, the area 91A of the front visual field image FV is divided into three areas, an area 91Aa at the center and areas 91Ab, 91Ac on both sides of the area 91Aa. Further, the area 91B of the right-hand side visual field image SV is divided into two areas, a left-hand area 91Ba and a right-hand area 91Bb. Moreover, the area 91C of the left-hand side visual field image SV is divided into two areas, a right-hand area 91Ca and a left-hand area 91Cb. In the front visual field image enhancement processing section 81 and the side visual field image enhancement processing sections 82, 83 described above, the front visual field image FV and the two side visual field images SV are each divided into a plurality of areas, here, the two or three areas.

An enhancement parameter corresponding to each scene in each divided area is inputted from the setting input section 25 and set in each of the front visual field image enhancement processing section 81 and the side visual field image enhancement processing sections 82, 83. Hence at least one of the enhancement level of the front visual field image FV and the enhancement levels of the two side visual field images SV is different in each of the areas of the front visual field image FV and the two side visual field images SV.

When the scene is selected or specified, the control section 21 supplies scene information of the specified observation scene to the front visual field image enhancement processing section 81 and the side visual field image enhancement processing sections 82, 83, and the front visual field image enhancement processing section 81 and the side visual field image enhancement processing sections 82, 83 execute the image enhancement processing on the respective areas by using a parameter in accordance with the observation scene, selected based on the supplied scene information.

In FIG. 19, as indicated by numbers in parentheses, the lowest enhancement level value ("1" in FIG. 19") is set in the area 91Aa at the center in the area 91A in the front visual field image FV, and the middle-degree enhancement level ("3" in FIG. 19) is set in the peripheral areas 91Ab, 91Ac on the left and right in the area 91A of the front visual field image FV. In the right-hand and left-hand side visual field images SV, the middle-degree enhancement level ("3" in FIG. 19) is set in the areas 91Ba, 91Ca close to the front visual field image FV. In the right-hand and left-hand side visual field images SV, the highest-degree enhancement level ("5" in FIG. 19) is set in the areas 91Bb, 91Cb distant from the front visual field image FV.

As shown in FIG. 19, the enhancement levels of the two areas close to each other in the two adjacent images (the areas 91Ab, 91Ba and the areas 91Ac, 91Ca in the case of FIG. 19) are set to the same value. This is intended so that, for example, when a lesion or the like moves from the side visual field image SV to the front visual field image FV, the appearance of the lesion does not look discontinuous.

Further, especially with the wide-angle endoscope, it is possible to observe an area only viewable from the deep side of the lumen when the view angle is wide, such as the back of layers of the intestinal wall, and when the highest enhancement level is set in an area in the side visual field image SV which is the farthest from the front visual field image FV (the areas 91Bb and the area 91Cb in the case of FIG. 19), a lesion on the back of the layers or the like can be displayed with image enhancement at the highest enhancement level, so that oversight in the lesion can be prevented.

That is, in the rectangular side visual field image SV, maximizing the enhancement level of the portion farthest from the front visual field image FV (specifically, a right end portion of the right-hand side visual field image SV and a left end portion of the left-hand side visual field image SV) facilitates finding of the lesion on the back of layers or the like.

Note that in FIG. 19, the areas 91A of the front visual field image FV and the areas 91B, 91C of the side visual field image SV are each divided into two or three areas, but may be divided into three areas or more, or four areas or more.
(Modification 6)

As Modification 6, the enhancement level of any one, any two, or all of the front visual field image FV and the two side visual field images SV may be set in accordance with the position of each pixel.

Figure 20:
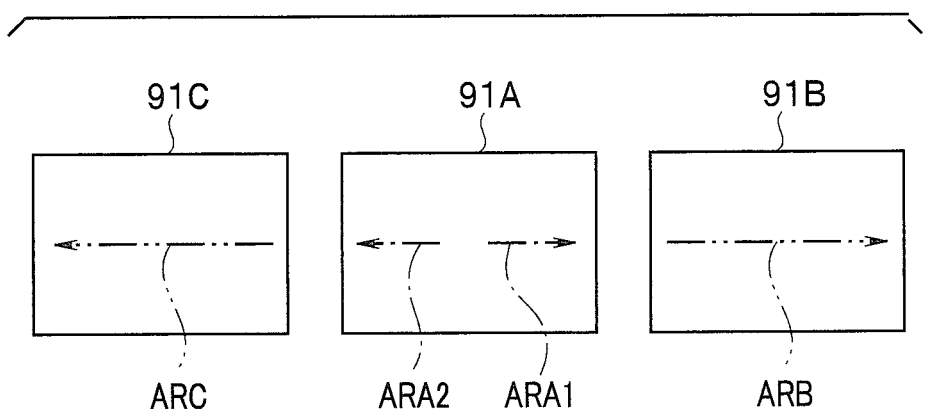
FIG. 20 is a view for describing an enhancement level that changes in accordance with a position of each pixel in each of the front visual field image FV and two side visual field images SV according to Modification 6 of the second embodiment of the present invention.

FIG. 20 is a view for describing the enhancement level that changes in accordance with the position of each pixel in each of the front visual field image FV and the two side visual field images SV.

As shown in FIG. 20, at each pixel in the area 91A of the front visual field image FV, the enhancement level is set in accordance with a distance from a center of the rectangle. For example, the enhancement level for each pixel in the area 91A of the front visual field image FV is set such that the enhancement level gradually increases from the center to the right-hand side periphery part along directions shown by arrows AR1, AR2 indicated by one-dot chain lines.

Further, the enhancement level for each pixel in the areas 91B, 91C of the two side visual field images SV is set such that the enhancement level gradually increases from a section close to the area 91A toward a section distant from the area 91A in each of the areas 91B, 91C, along directions shown by arrows ARB, ARC indicated by two-dot chain lines.

In order to strengthen the image enhancement of each side visual field image SV as distance from the front visual field image FV increases, the enhancement level for each pixel in each of the areas 91B, 91C of the side visual field images SV is set such that the enhancement level gradually increases along the directions shown by the arrows ARB, ARC indicated by the two-dot chain lines. That is, the enhancement level of each side visual field image SV continuously varies in accordance with the distance from the front visual field image FV. The enhancement level in each side visual field image SV is the highest in a position most distant from the front visual field image FV.

Especially by matching or substantially matching the enhancement level of the right-hand end portion of the front visual field image FV with the left-hand end portion of the right-hand side visual field image SV, and similarly by matching or substantially matching the enhancement level of the left-hand end portion of the front visual field image FV with the enhancement level of the right-hand end portion of the left-hand side visual field image SV, the enhancement levels of the front visual field image FV and the side visual field images SV continuously vary, whereby it is possible to eliminate an unnatural feeling at the time of viewing the front visual field image FV and the side visual field images SV.

Note that, although the enhancement level is set in accordance with the position of each pixel in both the front visual field image FV and the two side visual field images SV in FIG. 20, for example, one enhancement level may be set as a whole in the front visual field image FV and the enhancement level may be set in one of or both of the two side visual field images SV so as to gradually increase from a section close to the area 91A toward a section distant from the area 91A.
(Modification 7)

Although the enhancement level of each area is previously set for each observation scene in the embodiment and each of Modifications 5 and 6 described above, the previously set enhancement level may be made changeable during observation.

For example, when the display screen 5a as in FIG. 18 or FIG. 19 is displayed on the monitor 5, upon specification of a desired area, the operator may be able to change an enhancement level of the specified area to a desired level. It is possible to specify an area in which an enhancement level is to be changed and to change the enhancement level, by using the mouse or the like in the setting input section 25. For example, when the operator specifies the area 91A of the front visual field image FV with the mouse or the like and inputs a value with a keyboard, only the enhancement level of the area 91A is changed while the enhancement levels of the areas 91B, 91C of the side visual field images SV are not changed.

When the previously set enhancement level is changeable during observation, the operator can perform determination on the condition of the lesion, and the like, from more pieces of information.

(Modification 8)

Although the enhancement processing is performed on the previously set area in the embodiment described above, the enhancement processing may be performed only on a desired area in each area.

Although not shown, for example, a predetermined frame 63 as shown in FIG. 11 of Modification 4 of the first embodiment may be displayed under instruction of the user, and when the user instructs to move the frame 63 from the setting input section 25, the frame 63 may move in accordance with the instruction. An image with the enhancement processing performed only on the area in the frame 63 may be displayed, and an image with the enhancement processing not performed on an area other than the frame 63 may be displayed.

Further, each area may be previously divided into a plurality of areas, and in accordance with an instruction of the user, an area to be subjected to the enhancement processing may be made changeable among the plurality of areas.

Although not shown, for example as shown in FIG. 12 of Modification 4 of the first embodiment, the front visual field image FV and the two side visual field images SV are each divided into a plurality of areas, and the user selects any of the areas 91A, 91B, 91C to be subjected to the enhancement processing by using the mouse or the like in the setting input section 25, and selects and specifies any of the plurality of divided areas by using a predetermined button or the like in the setting input section 25, whereby an image with only the specified areas subjected to the image enhancement processing is displayed.

According to Modification 8, the operator can observe only the desired area in more detail to find a lesion or perform determination on the state of the lesion, or the like.

(Modification 9)

In the second embodiment and each modification described above, the mechanism for achieving the function of illuminating and observing the side is built in the insertion portion 6 along with the mechanism for achieving the function of illuminating and observing the front, but the mechanism for achieving the function of illuminating and observing the side may be a separate body removable from the insertion portion 6.

Figure 21:
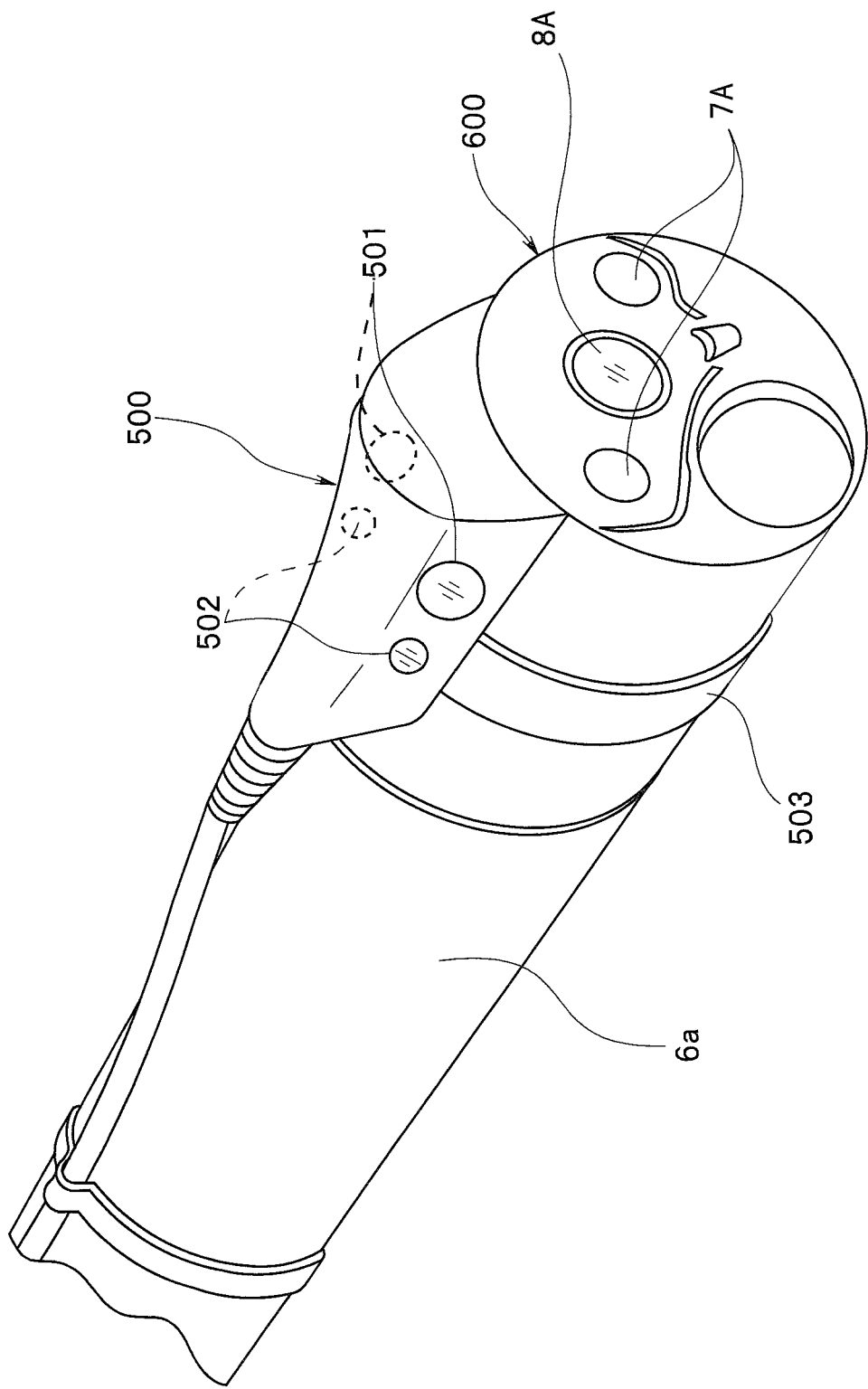
FIG. 21 is a perspective view of a distal end portion 6a of an insertion portion 6, to which a unit for side observation is attached, according to Modification 9 of the second embodiment of the present invention.

FIG. 21 is a perspective view of the distal end portion 6a of the insertion portion 6, to which a unit for side observation is attached, according to Modification 9. The distal end portion 6a of the insertion portion 6 includes a front visual field unit 600. A side visual field unit 500 is configured to be removable from the front visual field unit 600 with a clip portion 503.

The side visual field unit 500 includes two observation windows 501 for acquiring images in the horizontal direction and two illumination windows 502 for illumination in the horizontal direction.

The processor 3A and the like control the image pickup and illumination by the side visual field unit 500.

The second embodiment and each of Modifications 5 to 8 described above are also applicable to an endoscope system with such a removable side observation unit.

As above, according to the second embodiment and each of Modifications 5 to 9 described above, it is possible to provide an endoscope system capable of performing image enhancement processing on a plurality of visual field images each having a different role, the processing being suited for each role.

Note that each embodiment and each modification described above is an example of the endoscope system using white light, but each embodiment and each modification described above is also applicable to an endoscope system capable of performing endoscopy by using special light, such as narrow band observation and fluorescence observation. That is, the front visual field image and the side visual field image may be images obtained by irradiating the object with white light or may be images obtained by irradiating the object with light other than white light.

In the case of endoscopy using the special light, the image may become dark. When the image is dark, noise tends to be generated. Therefore, in such a case, application of each embodiment and each modification described above leads to reduction in generation of noise and prevention of oversight in a lesion.

As above, according to each embodiment and each modification described above, it is possible to provide an endoscope system capable of performing image enhancement processing on a plurality of visual field images each having a different role, the processing being suited for each role, and further to improve quality of the endoscopy.

Moreover, it is possible to perform the enhancement processing on an endoscope image at an enhancement level optimal for each view field or suitable for preference of the operator, thereby improving a rate of finding a lesion and diagnosability for the found lesion.

The present invention is not restricted to the embodiments described above, and various modifications, alternation, and the like can be made in a scope not changing the gist of the present invention.

What is claimed is:

1. An image processing apparatus for an endoscope, comprising:
a processor comprising hardware, the processor being configured to:
perform first enhancement processing on a front image acquired from a front area in a subject by using an endoscope including an insertion portion which is inserted into the subject, and
perform second enhancement processing on a side image acquired from a side area located lateral to the front area,
wherein
the processor individually sets a first enhancement level of the first enhancement processing and a second enhancement level of the second enhancement processing, and
the processor sets the second enhancement level in the side image such that a degree of an image enhancement becomes higher as distance from the front image increases.

2. The image processing apparatus for an endoscope according to claim 1, wherein in a screening scene that is a scene in which observation is performed during removal of the insertion portion in examination with the endoscope, the processor individually sets the first enhancement level and the second enhancement level such that the degree of the image enhancement becomes stronger higher as distance from the front image increases, with respect to an insertion scene in which the insertion portion is inserted inside the subject.

3. The image processing apparatus for an endoscope according to claim 1, wherein the processor sets the first enhancement level and the second enhancement level such that a degree of the second enhancement processing is at an enhancement level equal to or higher than a degree of the first enhancement processing.

4. The image processing apparatus for an endoscope according to claim 1, wherein, when an observation scene in examination with the endoscope is a screening scene that is a scene in which observation is performed during removal of the insertion portion, the processor sets the first enhancement level and the second enhancement level such that an amount of enhancement on the side image is relatively larger than an amount of enhancement on the front image.

5. The image processing apparatus for an endoscope according to claim 1, wherein the processor individually sets the first enhancement level and the second enhancement level to change in accordance with a screening scene being a scene in which observation is performed during removal of the insertion portion, a magnifying scene in which magnifying observation is performed on the front image, and a treatment scene in which treatment is performed on the subject caught in the front image, in examination with the endoscope.

6. The image processing apparatus for an endoscope according to claim 5, wherein, when the observation scene in the examination with the endoscope is the magnifying scene or the treatment scene, the processor sets the first enhancement level and the second enhancement level such that an amount of enhancement on the front image is relatively larger than an amount of enhancement on the side image.

7. The image processing apparatus for an endoscope according to claim 5, wherein the processor sets the first enhancement level such that an amount of enhancement on the front image at a time when the observation scene in the examination with the endoscope is the treatment scene is relatively small with respect to an amount of enhancement on the front image at a time when the observation scene is the magnifying scene.

8. The image processing apparatus for an endoscope according to claim 1, wherein the processor outputs, to a display, information representing an observation scene in examination with the endoscope added to the front image that undergoes the first enhancement processing and the side image that undergoes through the second enhancement processing.

9. The image processing apparatus for an endoscope according to claim 1, wherein the processor outputs, to a display, information representing the first enhancement level and the second enhancement level added to the front image that undergoes the first enhancement processing and the side image that undergoes the image second enhancement processing.

10. The image processing apparatus for an endoscope according to claim 1, wherein the processor sets the first enhancement level individually for each divided area formed by dividing the front image into a plurality of areas and sets the second enhancement level individually for each divided area formed by dividing the side image into a plurality of areas.

11. The image processing apparatus for an endoscope according to claim 1, wherein the first enhancement processing and the second enhancement processing are at least one of structure enhancement to enhance contrast of an image or a rate of change in color tone, contour enhancement to thickly enhance a portion with contrast of an image or a change in color tone, and hue enhancement to enhance hue of the image.

12. The image processing apparatus for an endoscope according to claim 1, further comprising a light source configured to emit illumination light to the front area and the side area.

13. An endoscope system comprising:
the image processing apparatus for an endoscope according to claim 1;
a front observation optical system configured to form an optical image of the front area;
a side observation optical system configured to form an optical image of the side area;
a first image sensor configured to pick up the optical image of the front area and generate the front image; and
a second image sensor formed as a separate body from the first image sensor and configured to pick up the optical image of the side area and generate the side image.

* * * * *